US 7,289,655 B2

(12) United States Patent
Kitabayashi

(10) Patent No.: US 7,289,655 B2
(45) Date of Patent: Oct. 30, 2007

(54) DEVICE FOR INSPECTING ILLUMINATION OPTICAL DEVICE AND METHOD FOR INSPECTING ILLUMINATION OPTICAL DEVICE

(75) Inventor: Masashi Kitabayashi, Horigane-mura (JP)

(73) Assignee: Seiko Epson Corporation, Tokyo (JP)

( * ) Notice: Subject to any disclaimer, the term of this patent is extended or adjusted under 35 U.S.C. 154(b) by 715 days.

(21) Appl. No.: 10/189,445

(22) Filed: Jul. 8, 2002

(65) Prior Publication Data
US 2003/0063789 A1 Apr. 3, 2003

(30) Foreign Application Priority Data
Aug. 29, 2001 (JP) ............... 2001-259839

(51) Int. Cl.
G06K 9/00 (2006.01)
H04N 7/18 (2006.01)
H04N 9/47 (2006.01)
G01N 21/00 (2006.01)
G01B 9/08 (2006.01)

(52) U.S. Cl. ............ 382/141; 348/92; 356/239.1; 356/239.2; 356/239.3; 356/239.4; 356/239.5; 356/239.6; 356/239.7; 356/239.8; 356/391

(58) Field of Classification Search ......... 382/141
See application file for complete search history.

(56) References Cited

U.S. PATENT DOCUMENTS 5,517,310 A * 5/1996 Paquette ............... 356/615
5,694,479 A * 12/1997 Guering et al. ......... 382/141
6,148,097 A * 11/2000 Nakayama et al. ...... 382/141

FOREIGN PATENT DOCUMENTS

| JP | A-05-149824 | 6/1993 |
|----|-------------|--------|
| JP | A 6-204565 | 7/1994 |
| JP | A 8-15090 | 1/1996 |
| JP | A-11-313346 | 11/1999 |
| JP | A 2000-136982 | 5/2000 |
| JP | A-2002-328205 | 11/2002 |

* cited by examiner

Primary Examiner—Andrew W. Johns
Assistant Examiner—Damon Conover
(74) Attorney, Agent, or Firm—Oliff & Berridge, PLC

(57) ABSTRACT

The invention provides a device to inspect an illumination optical device and a method to inspect an illumination optical device that make it possible to efficiently inspect illumination optical devices and to control manufacturing cost. A lens array inspecting device is provided with a light source device to emit a parallel luminous flux, lens array holders to retain lens arrays, which are test objects that split the parallel luminous flux into a plurality of partial luminous fluxes, and a ground glass on which the optical images of the luminous fluxes emitted through the lens arrays are projected. On the ground glass, a parting frame appropriate to a design illumination region is formed. Therefore, whether the lens arrays are defective or non-defective can be determined by checking whether the optical images projected onto the ground glass include the area of the parting frame.

5 Claims, 20 Drawing Sheets

(A)

(B)

DEVICE FOR INSPECTING ILLUMINATION OPTICAL DEVICE AND METHOD FOR INSPECTING ILLUMINATION OPTICAL DEVICE

BACKGROUND OF THE INVENTION

1. Field of Invention

The present invention relates to a apparatus for inspecting an illumination optical device. In particular, the invention relates to an apparatus for inspecting the optical characteristics of an illumination optical device constituting an illumination optical system that condenses a luminous flux emitted from a light source lamp to form an optical image. The invention also relates to a method for inspecting a lens array serving as the illumination optical device.

2. Description of Related Art

Projectors can be used for presentations or the like. Projectors can be equipped with a light source lamp, an electro-optical device that modulates a luminous flux emitted from the light source lamp according to image information, and a projection optical system to enlarge and projecting the luminous flux modulated by the electro-optical device.

In such a projector, an illumination optical system is frequently disposed between the light source lamp and the electro-optical device to evenly illuminate an image forming region of the electro-optical device by the luminous flux emitted from the light source lamp.

A related art illumination optical system uses a lens array acting as a luminous flux splitting device constituted by a plurality of planar semicircular (plano-convex lenses) small lenses arranged in a matrix pattern in the plane orthogonal to the direction in which light is emitted.

In such a construction, the illumination optical system splits the luminous flux emitted from the light source lamp into a plurality of partial luminous fluxes by a plurality of small lenses making up the lens array, to superimpose the partial luminous fluxes in the image forming region of the electro-optical device so as to evenly illuminate the image forming region. This makes it possible to obtain a sharp projection image free of uneven luminance.

The lens array is fabricated as follows. First, a molten glass or resin material is poured into a mold having the configuration for the plurality of small lenses making up the lens array so as to mold the small lenses, or softened glass is press-molded using a mold to obtain the small lenses. Then, these plural small lenses are disposed at predetermined positions and subjected to heat treatment so as to fabricate a lens array formed of the integrated small lenses.

SUMMARY OF THE INVENTION

However, the lens array fabricated as described above is likely to have the individual small lenses deformed due to the heat treatment or misaligned due to a difference in thermal expansion or shrinkage, or the like. For this reason, there are cases where the lens array does not have optical characteristics as per predetermined specifications, and therefore the lens array fails to provide sharp projected images.

Hence, in the manufacture of the projector, after all components are assembled to complete the projector, an inspection is performed to determine whether the lens array exhibits satisfactory optical characteristics.

However, in such an inspection process, if a lens array proves to have an inadequate function, then the finished projector that has been assembled with considerable effort has to be disassembled to replace the lens array. This complicated inspection operation has led to an increase in the manufacturing cost.

The same problem applies not only to a lens array, but also to other luminous flux splitting devices, such as a rod, a condensing device to turn the luminous flux emitted from a light source lamp into a parallel beam, and other illumination optical devices, such as a polarization converting device.

The present invention provides a device to inspect an illumination optical device and a method to inspect an illumination optical device that allows efficient inspection of an illumination optical device to be accomplished and manufacturing cost to be controlled.

A device to inspect an illumination optical device according to a first aspect of the present application is adapted to detect a luminous flux emitted from a light source through an illumination optical device to inspect the optical characteristics of the illumination optical device. The device includes a holder to hold the illumination optical device as an object to be inspected, and a projection plate on which an optical image of the luminous flux emitted from the illumination optical device held by the holder is projected. A parting frame based on an illumination region of the illumination optical device is formed on the projection plate.

The illumination optical device may be a condensing device to turn a luminous flux emitted from a light source lamp into a parallel luminous flux, a luminous flux splitting device, such as a lens array or rod, and various types of optical devices, such as a polarization converting device, or may be a combination of these devices.

The optical characteristics of an illumination optical device to be inspected may be, for example, the focal lengths, the positions of the optical axes, the shapes, etc. of the individual small lenses making up the lens array when a lens array, for example, is inspected as the illumination optical device. To inspect a condensing device as an illumination optical device, the parallelism or the like of a luminous flux to be emitted may be an optical characteristic to be inspected.

However, the optical characteristics of such illumination optical devices are considered acceptable as long as the optical image formed by the illumination optical system equipped with all illumination optical devices is as per specifications. Hence, whether the optical characteristics are acceptable may be determined by checking whether the optical image has a predetermined luminance in a predetermined range.

According to the first invention described above, the parting frame based on an illumination region is formed, so that it can be determined that the illumination optical device is defective if any portion where the luminance is lower than a designed luminance is detected in the parting frame, permitting easy inspection of the optical characteristics of an illumination optical device.

Thus, the optical characteristics of the illumination optical device can be inspected simply by installing an illumination optical device on a holder. This obviates the need to inspect an illumination optical device after all components are assembled into a finished projector with considerable effort, as in the related art, so that load of the inspection operation can be reduced and the manufacturing cost can be controlled.

Preferably, the device to inspect an illumination optical device in accordance with the present invention is equipped with a light source device to supply a luminous flux to the illumination optical device.

With this arrangement, a constant luminous flux is always emitted from the light source device, so that no error from the light source device need to be considered, and the illumination optical device as an object to be inspected can be inspected with higher accuracy.

Preferably, the light source device is constructed to emit a parallel luminous flux, and is movable forward/backward with respect to an illumination optical axis of the parallel luminous flux to be emitted.

With this arrangement, even if the shape, size, etc. of an illumination optical device as an object to be inspected changes, the light source device can be moved forward or backward in the direction of an illumination optical axis according to such a change, thereby permitting easy adjustment of the optical distance. The arrangement, therefore, is able to accommodate a plurality of types of illumination optical devices.

Preferably, the holder and the projection plate are constructed as an integral unit for setting an object to be inspected, and the unit to set the object to be inspected is provided as many as a plural number according to the type of optical apparatus in which an illumination optical device, which is a test object, is used.

With this arrangement, considering that the size, disposition, etc. of the illumination optical device differ, depending upon the type of optical apparatus with which the illumination optical device is used, it is not necessary to bother to change the disposition or the like of the illumination optical device each time the type of optical apparatus changes. Thus, the illumination optical device to be inspected can be easily disposed, further reducing the load of the inspecting operation.

Preferably, the device to inspect an illumination optical device is equipped with an image detecting device to detect an optical image projected onto the projection plate and the parting frame. The image detecting device is equipped with an image pickup device, an image capturing device to capture an optical image detected by the image pickup device, and an image processing device to process the optical image captured by the image capturing device.

With this arrangement, the image detecting device is provided that is adapted to detect a projected optical image and a parting frame by the image pickup device, capture the detected optical image by the image capturing device, and process the captured optical image by the image processing device. Hence, the luminance of the optical image can be automatically measured. This allows pass/fail to be easily determined simply by comparing the detected parting frame with the processed optical image, thus permitting the load of the inspection operation to be reduced.

Preferably, the image processing means is equipped with a luminance value determining unit to determine the luminance value of the optical image captured from the image pickup device.

With this arrangement, whether the optical image projected in the parting frame has not less than a predetermined luminance value can be automatically determined, thus permitting the load of the inspection operation to be reduced.

Preferably, the illumination optical device is a luminous flux splitting device to split a luminous flux emitted from a light source into a plurality of partial luminous fluxes.

With this arrangement, considering the fact that the yield of luminous flux splitting devices, in particular, among illumination optical devices is low, the yield of the finished products can be efficiently enhanced simply by inspecting the luminous flux splitting devices, thus allowing even easier inspection to be achieved.

A method to inspect an illumination optical device according to a second aspect of the present application detects a luminous flux emitted from a light source through the illumination optical device and inspects the optical characteristics of the illumination optical device. The method includes an optical image forming procedure for forming an optical image of the luminous flux emitted through the illumination optical device onto a projection plate on which a parting frame is formed in association with an illumination region of the illumination optical device, an image capturing procedure for capturing, by using an image pickup device and an image capturing device, the optical image formed by the optical image forming procedure, a luminance value acquiring procedure for acquiring a luminance value of the captured optical image, and a pass/fail determining procedure for determining whether the illumination optical device is non-defective or defective on the basis of the luminance value acquired in the luminance value acquiring procedure.

According to the second aspect of the invention, the advantage similar to the that of the first aspect can be obtained. More specifically, an illumination optical device can be easily and automatically inspected simply by disposing an illumination optical device, which is a test object, on a holder and by starting the inspection. This permits the load of the inspecting operation to be reduced.

Preferably, the pass/fail determining procedure includes a luminance change position acquiring step for acquiring a luminance change position on the projection plate where the luminance value acquired on a scanning line along the parting frame changes at a preset luminance threshold value, and a luminance change position determining step for determining whether the acquired luminance change position is within the parting frame.

With this arrangement, it can be easily determined whether the luminance change position is within the parting frame simply by performing the determination in sequence along a scanning line, permitting inspection time to be shortened.

A method to inspect an illumination optical device according to a third aspect of the present application detects a luminous flux emitted from a light source through the illumination optical device so as to inspect the optical characteristics of the illumination optical device. The method includes an optical image forming procedure for forming an optical image of the luminous flux emitted through the illumination optical device onto a projection plate on which a parting frame is formed in association with an illumination region of the illumination optical device, an image capturing procedure for capturing an image, by using an image pickup device and an image capturing device, the optical image formed by the optical image forming procedure, a luminance value acquiring procedure for acquiring a luminance value of the captured optical image, an illumination region acquiring procedure for acquiring a region where the acquired luminance values are a preset luminance threshold value or more as the illumination region of the optical image, an illumination margin calculating procedure for calculating an illumination margin on the basis of the acquired illumination region and an illuminated region defined by the parting frame, a difference amount calculating procedure for calculating the amount of a difference between centers on the basis of the center of illumination region obtained by the illumination region acquiring procedure and the center of the illuminated region obtained by the parting frame, and a pass/fail determining procedure for determining whether the illumination optical device is non-defective or defective on the basis of the calculated illumination margin and the amount of the difference between the centers.

According to the third aspect of the invention, an illumination region of the optical image projected onto a projection plate is acquired by the illumination region acquiring procedure, the illumination margin is calculated according to the illumination margin calculating procedure on the basis of the illumination region and the illuminated region defined by the parting frame, and the central difference amount is calculated on the basis of the center of the illumination region and the center of the illuminated region. Then, whether the illumination optical device is non-defective or defective is determined on the basis of the calculated illumination margin and central difference amount according to the pass/fail determining procedure.

Since the determination is performed as described above, an illumination optical device can be inspected easily and automatically simply by disposing the illumination optical device, which is the object to be inspected, on a holder or the like and beginning the inspection. This permits the load of the inspecting operation to be reduced.

In the pass/fail determining procedure in the second invention, if an improperly set illumination optical device causes the luminance change position of the optical image projected onto the projection plate to enter the parting frame, then the illumination optical device that should be determined as non-defective will be determined defective.

On the other hand, in the pass/fail determining procedure in the third aspect of the invention, if, for example, predetermined values of the illumination margin and the amount of the difference between centers that cause the illumination optical devices to be determined defective due to misaligned setting of the illumination optical devices are established in advance, then accurate determination of an illumination optical device that would have been determined as defective due to misaligned setting can be achieved on the basis of a calculated illumination margin and amount of the difference between centers. Thus, illumination optical devices that may be erroneously determined as defective can be securely determined non-defective, permitting the yield of illumination optical devices to be enhanced.

Preferably, the pass/fail determining procedure determines that the illumination optical device is non-defective if the illumination margin is larger than a predetermined value and the amount of the difference between the centers is a value within a predetermined range.

With this arrangement, even in the case, for example, of an illumination optical device that would be determined as defective due to misaligned setting of the illumination optical device, pass/fail can be easily determined simply by establishing predetermined values of an illumination margin and the amount of the difference between centers in advance, as described above.

Preferably, the pass/fail determining procedure determines that the illumination optical device is misaligned in installation if the illumination margin is larger than a predetermined value, and the amount of the difference between the centers is a value within a predetermined range.

With this arrangement, it can be securely and easily determined whether an illumination optical device is merely set in a misaligned fashion simply by setting predetermined values of the illumination margin and the amount of the difference between centers.

Alternatively, in the method for inspecting an illumination optical device, an orthogonal coordinate system formed of an X-axis and a Y-axis may be set in a plane orthogonal to an illumination optical axis of the luminous flux, and the illumination margin calculating procedure may calculate the illumination margin in the direction of the X-axis on the basis of the distance of the illumination region in the direction of the X-axis and the distance of the illuminated region in the direction of the X-axis, and calculate the illumination margin in the direction of the Y-axis on the basis of the distance of the illumination region in the direction of the Y-axis and the distance of the illuminated region in the direction of the Y-axis.

If, for example, the illumination region and the illuminated region are rectangular, then the X-axis and the Y-axis may be set along the sides orthogonal to each other in the rectangle.

If an XY coordinate is established, for example, along the rectangular sides, as discussed above, then distances in the respective axial directions in the illumination region can be determined for the X-axis direction and the Y-axis direction, respectively, on the basis of the XY coordinates on opposing two sides from each XY coordinate of a plurality of points (pixels) constituting each side on each side in the four sides along the axial directions in the rectangular illumination region.

In such a case, the illumination margin in the X-axis direction is determined, for example, as described hereinafter. More specifically, first, the distance in the X-axis direction in the illumination region is determined from each X coordinate of each of two sides that extend in the direction of the Y-axis and oppose each other. Then, the difference between the distance in the X-axis direction in the illumination region and the distance in the X-axis direction in the illuminated region. The illumination margin, i.e., the illumination margin in the X-axis direction, of each side can be easily calculated merely by halving the determined difference. In the same manner, the illumination margin in the Y-axis direction can be easily calculated.

The illumination margin calculating procedure may calculate the illumination margin on the basis of the areas of the illumination region and the illuminated region.

In this case, the illumination margin can be easily calculated on the basis of the difference between the areas of the illumination region and the illuminated region.

DETAILED DESCRIPTION OF PREFERRED EMBODIMENTS

The present invention will be further illustrated with embodiments below in conjunction with accompanying drawings.

First Embodiment

Figure 1:
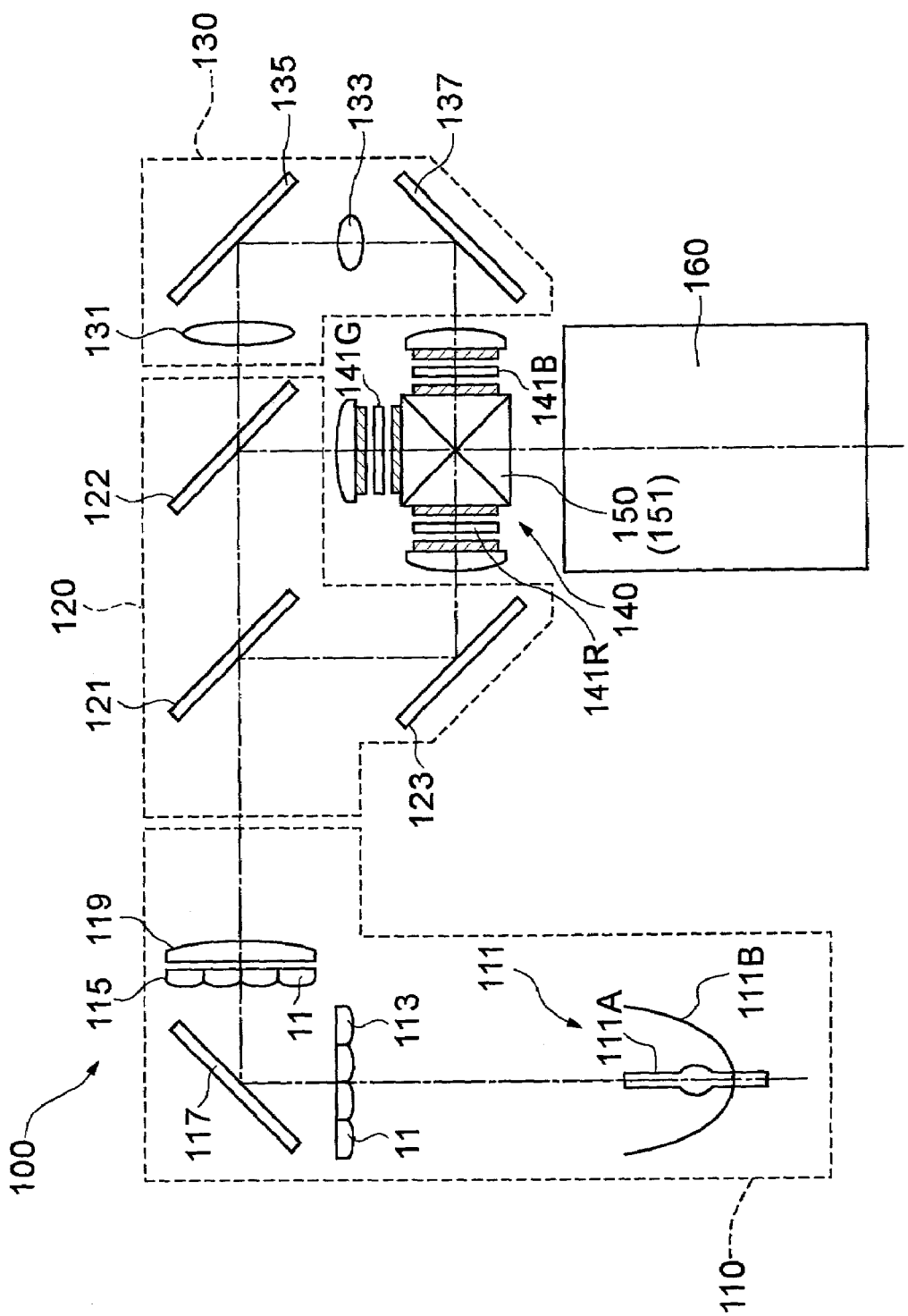
FIG. 1 is a schematic showing a projector that uses an illumination optical device to be inspected by an inspecting device in accordance with each embodiment of the present invention.

<1> Structure of a Projector in which a Lens Array is Used as an Illumination Optical Device FIG. 1 is a schematic illustrating the structure of a projector 100 in which a lens array is adopted as an illumination optical device to be inspected by the device for inspecting an illumination optical device in accordance with a first embodiment of the present invention.

The projector 100 is equipped with an integrator illumination optical system 110, a color separating optical system 120, a relay optical system 130, an electro-optical device 140, a color synthesizing optical system 150, and a projection optical system 160.

The integrator illumination optical system 110 is equipped with a light source device 111 including a light source lamp 111A and a reflector 111B, a first lens array 113, a second lens array 115, a reflection mirror 117, and a superimposing lens 119.

A luminous flux from the light source lamp 111A is emitted as a parallel luminous flux whose outgoing direction is made uniform by a reflector 111B, split into a plurality of partial luminous fluxes through the first lens array 113, bent by 90 degrees in its outgoing direction by the return reflection mirror 117, then formed into images in the vicinity of the second lens array 115. The individual partial luminous fluxes emitted from the second lens array 115 enters the incident surface of the superimposing lens 119 in a subsequent stage such that its central axis (main beam) is perpendicular to the incident surface of the superimposing lens 119. Furthermore, the plurality of partial luminous fluxes emitted from the superimposing lens 119 are superimposed on three liquid crystal panels 141R, 141G, and 141B that constitute the electro-optical device 140, which will be discussed hereinafter.

The color separating optical system 120 is equipped with two dichroic mirrors 121, 122 and a reflection mirror 123, and separates the plurality of partial luminous fluxes emitted from the integrator illumination optical device 110 into three color beams of red, green, and blue by the mirrors 121, 122, and 123.

The relay optical system 130 is equipped with an incident lens 131, a relay lens 133, and reflection mirrors 135, 137, and guides a color beam, e.g., a blue beam B, separated by the color separating optical system 120 to the liquid crystal panel 141B.

The electro-optical device 140 is equipped with three liquid crystal panels 141R, 141G, and 141B. These use, for example, polysilicon TFTs as the switching elements. The individual color beams separated by the color separating optical system 120 are modulated by the three liquid crystal panels 141R, 141G, and 141B according to image information so as to form optical images.

The color synthesizing optical system 150 is equipped with a cross dichroic prism 151, and functions to synthesize the images modulated for the respective color beams emitted from the three liquid crystal panels 141R, 141G, and 141B so as to form a color image.

In the cross dichroic prism 151, a dielectric multilayer film that reflects red beams and a dielectric multilayer film that reflects blue beams are formed substantially in an X shape along the interfaces of four rectangular prisms, and the three color beams are synthesized by these dielectric multilayer films. Then, the color image synthesized by the color synthesizing optical system 150 is emitted from the projection optical system 160, and enlarged and projected onto a screen.

<2> Structure of a Lens Array, which is a Test Object

Figure 2:
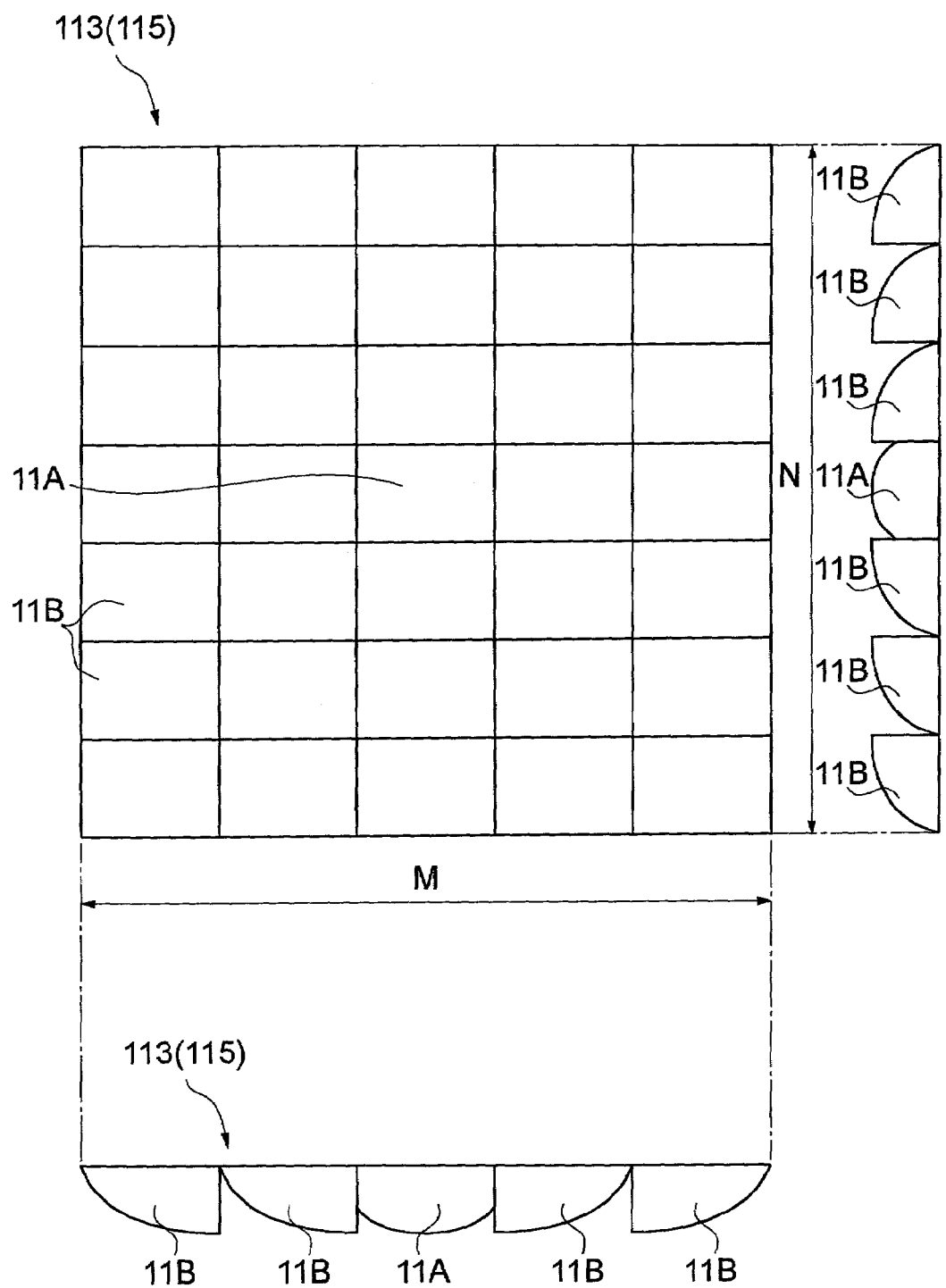
FIG. 2 is a front view and a side view showing the structure of the illumination optical device in each embodiment.

The first lens array 113 adopted in the foregoing projector 100 is constructed of two types of small lenses 11A and 11B that are arranged in M lines and N columns in a matrix pattern in a plane orthogonal to the direction in which the light of the small lenses 11A and 11B is emitted, as shown in FIG. 2.

More specifically, the small lenses 11A are disposed in a central portion of the first lens array 113, and the small lenses 11B are disposed around the small lenses 11A to surround the small lenses 11A. The small lenses 11A and 11B split the parallel luminous flux emitted from the light source device 111 into a plurality (M×N pieces) of partial luminous fluxes, and the split partial luminous fluxes are formed into an image in the vicinity of the second lens array 115, as previously described.

Figure 3:
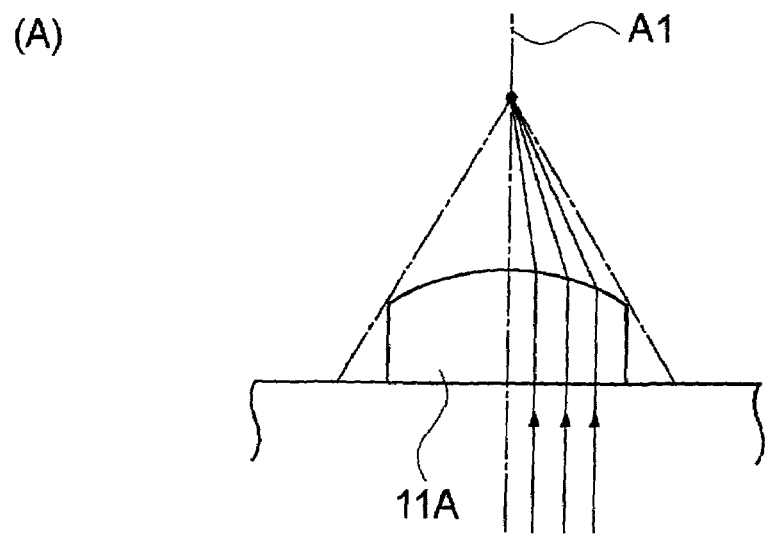
FIGS. 3(A) and 3(B) are partial plan views showing the focal position of the illumination optical device in each embodiment.
Figure 3:
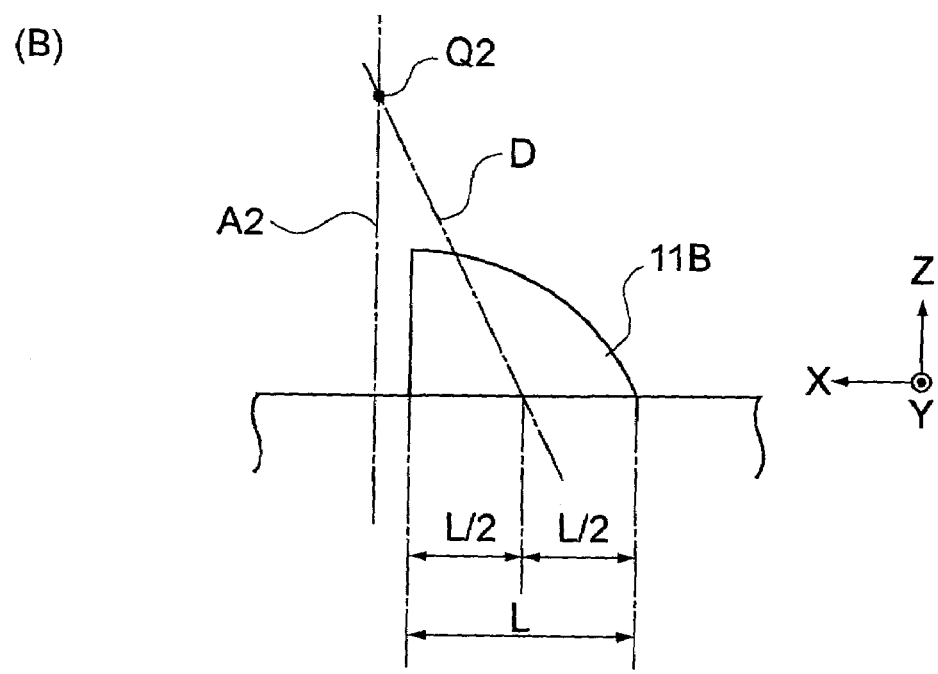

The shape of the small lenses 11A is set to be substantially similar, as viewed from the front, to the shape of the image forming regions of the liquid crystal panels 141R, 141G, and 141B making up the electro-optical device 140. For instance, if the aspect ratio (the vertical-to-horizontal dimensional ratio) of the liquid crystal panels 141R, 141G, and 141B is 4:3, then the aspect ratio of the small lenses 11A is also set to 4:3. The small lenses 11A are formed into a planar semicircular shape, and the position of the optical axis thereof is set at the center of the small lens 11A (chain line A1), as shown in FIG. 3(A).

Meanwhile, as shown in FIG. 2, the shape of the small lenses 11B is set to be substantially similar, as viewed from the front, to the shape of the image forming regions of the liquid crystal panels 141R, 141G, and 141B making up the electro-optical device 140, as in the case of the small lenses 11A. The small lenses 11B are formed into a planar arc shape, and are decentered lenses in which the position of the optical axis thereof is deviated from the geometrical center of the small lenses 11B, as shown in FIG. 3(B).

More specifically, the position of the optical axis is deviated from the geometrical center by predetermined dimensions in the X-axis direction and the Y-axis direction. The position of the focal point of the small lenses 11B is an intersection Q2 of a geometrical centerline D passing the geometrical central position of the small lenses 11B (the central position on the plane of each small lens 11B) and an optical axis A2 passing the foregoing optical axis position. The geometrical central position of the small lenses 11B (the central position on the plane of each small lens 11B) is the position that is L/2, that is, half of a width dimension L of the small lens 11B in the direction orthogonal to the optical axis A2. Although not shown in FIG. 2 and FIGS. 3(A) and 3(B), the amount of decentering of the small lenses 11B (the distance between the geometrical centerline D and the optical axis A2) increases as the distance thereof from the small lenses 11A increases.

As in the case of the first lens array 113 discussed above, the second lens array 115 is also constructed of two types of small lenses 11A and 11B arranged in a matrix pattern of M lines and N columns. As previously mentioned, however, the second lens array 115 is provided to cause the major beam of the plural partial luminous fluxes split by the first lens array 113 to perpendicularly enter the incident surface of the superimposing lens 119 in a subsequent stage. Therefore, the second lens array 115 does not have to have the same construction as the first lens array 113. For example, the small lenses may have various other shapes as long as they allow the plurality of partial luminous fluxes to perpendicularly enter the incident surface of the superimposing lens 119. More specifically, the small lenses constituting the second lens array 115 do not have to have a similar shape to the aspect ratio in the image forming region of the liquid crystal panels 141R, 141G, and 141B, as in the case of the first lens array 113. In this embodiment, for the convenience of fabrication, the small lenses 11A and 11B are arranged in the matrix pattern of M lines and N columns to make up the second lens array 115.

The first lens array 113 and the second lens array 115 are formed in a manner that a molten glass or resin material is poured into a mold having the configurations for the plurality of small lenses 11A and 11B, or softened glass is press-molded using molds according to the configurations of the plurality of the small lenses 11A and 11B, then slowly cooled.

Hence, the small lenses 11A and 11B making up the first lens array 113 and the second lens array 115 may deform, or a problem, such as misalignment, of the small lenses 11A and 11B in the first lens array 113 and the second lens array 115 may take place. For this reason, changes in the optical characteristics of the first lens array 113 and the second lens array 115 caused by the above problems must be checked by using an inspecting device against designed optical characteristics.

To inspect the first lens array 113, a standard sample that satisfies a predetermined specification is used for the second lens array 115. Conversely, to inspect the second lens array 115, a standard sample that satisfies a predetermined specification is used for the first lens array 113. For this reason, the first lens array 113 and the second lens array 115, which are test objects, are provided with standard samples that satisfy the predetermined specifications.

<3> Structure of the Lens Array Inspecting Device

Figure 4:
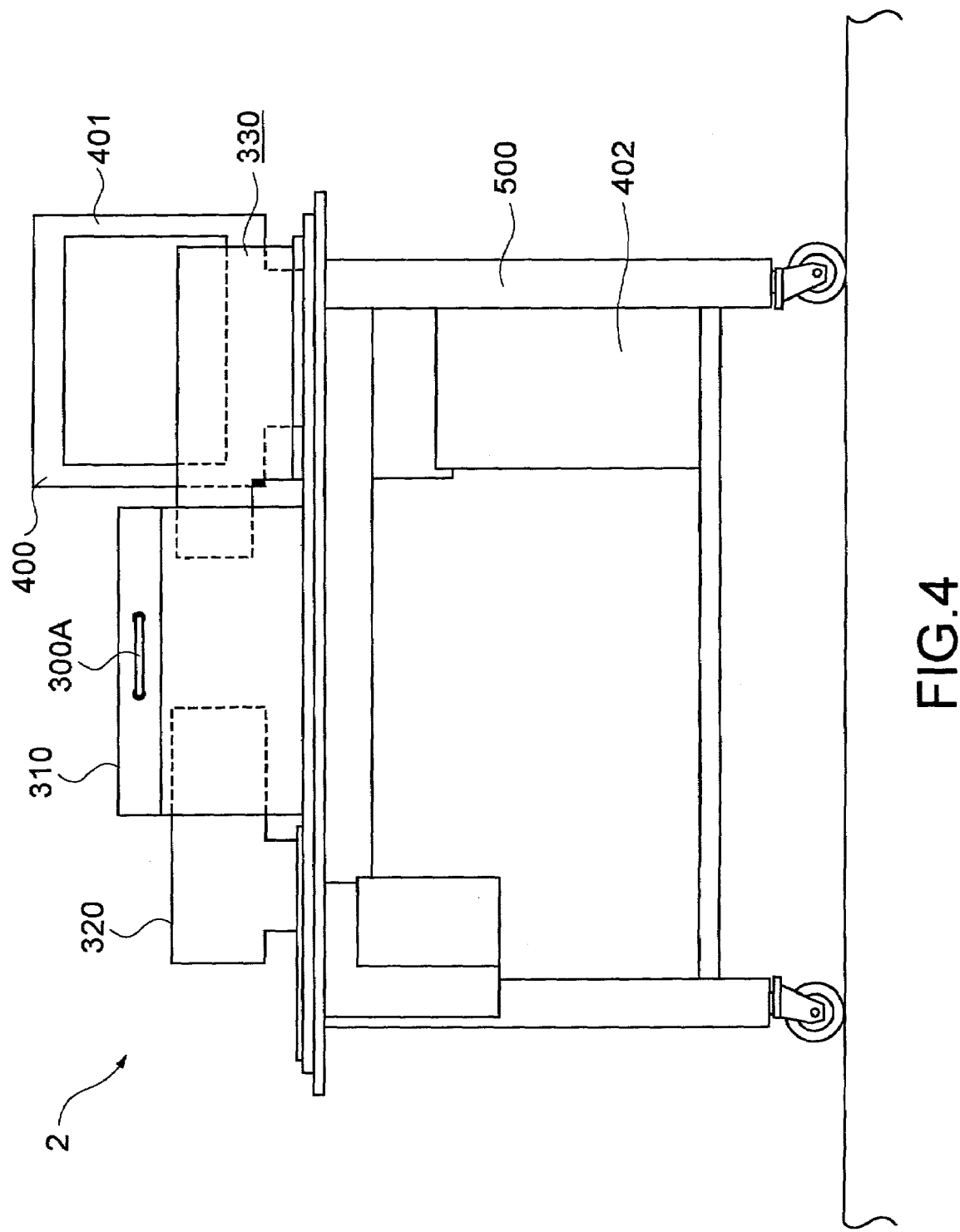
FIG. 4 is a front view showing the appearance of the inspecting device in each embodiment.

FIG. 4 shows a lens array inspecting device 2 to inspect the first lens array 113 and the second lens array 115 discussed above.

The lens array inspecting device 2, which is the device to inspect an illumination optical device, is provided with a detector 310, a light source device 320, an image processor 330, and a mounting base 500 for supporting the component units, as shown in FIG. 4.

Figure 5:
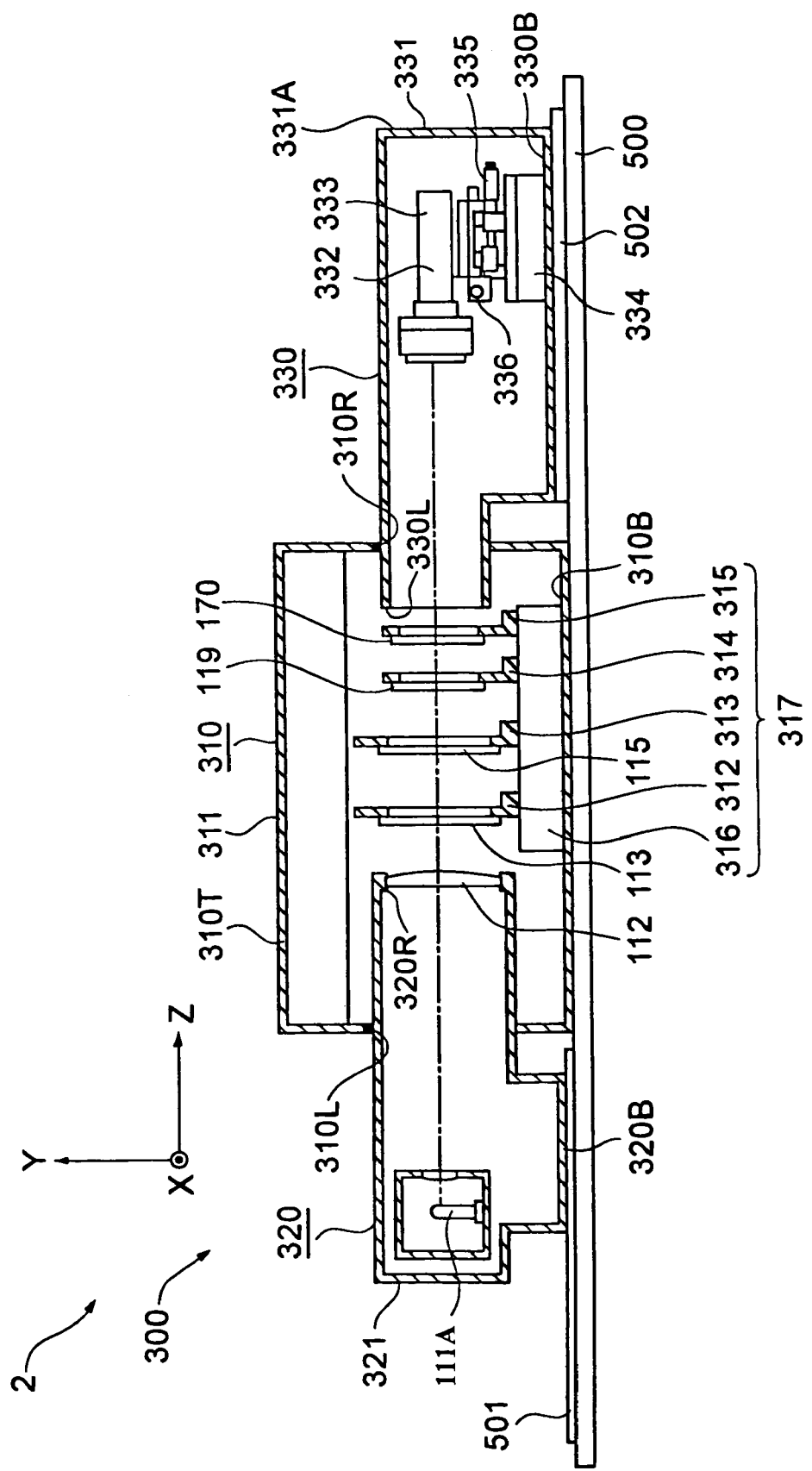
FIG. 5 is a front view showing the structure of the inspecting device in each embodiment.

As shown in FIG. 5, the detector 310 functions as a dark box covered with a shielding plate, and is constituted by a substantially rectangular parallelepiped case 311 having a cover 310T with a handle 300A (FIG. 4) formed thereon, and a test object setting unit 317 fixedly disposed on a bottom surface 3101B inside the case 311.

In the case 311, a left opening 310L in which the light source device 320 is inserted is formed in the left side surface (left side in FIG. 5) thereof, and a right opening 310R in which the image processor 330 to be discussed hereinafter is inserted is formed in the right side surface (right side in FIG. 5) thereof.

The cover 310T is circularly movable in its radial direction about an axis in a Z-axis direction by a hinge, which is not shown. The upper portion of the detector 310 can be opened and closed by circularly moving the cover 310T by holding the handle 300A, thus allowing the test object setting unit 317, which is placed therein, to be easily replaced.

The test object setting unit 317 is formed of a first lens array holder 312 to which the first lens array 113, as a test object, is set, a second lens array holder 313 to which the second lens array 115, as a test object, is set, a superimposing lens holder 314 to which the superimposing lens 119 is attached, a ground glass 170 serving as a projection plate, a ground glass holder 315 to which the ground glass 170 is attached, and a rectangular parallelepiped retaining base 316 to which the holders 312 through 315 are mounted, these components being integrated into one assembly.

As the test object setting unit 317, a plurality of types of test object setting units for different sizes and dispositions of the holders 312 through 315 are prepared to accommodate the types of projectors to be used.

The superimposing lens 119, which is a general condensing lens, condenses the major beams of the partial luminous fluxes emitted through the second lens array 115 and form optical images 600 (FIG. 12) on the surface of the ground glass 170.

Figure 6:
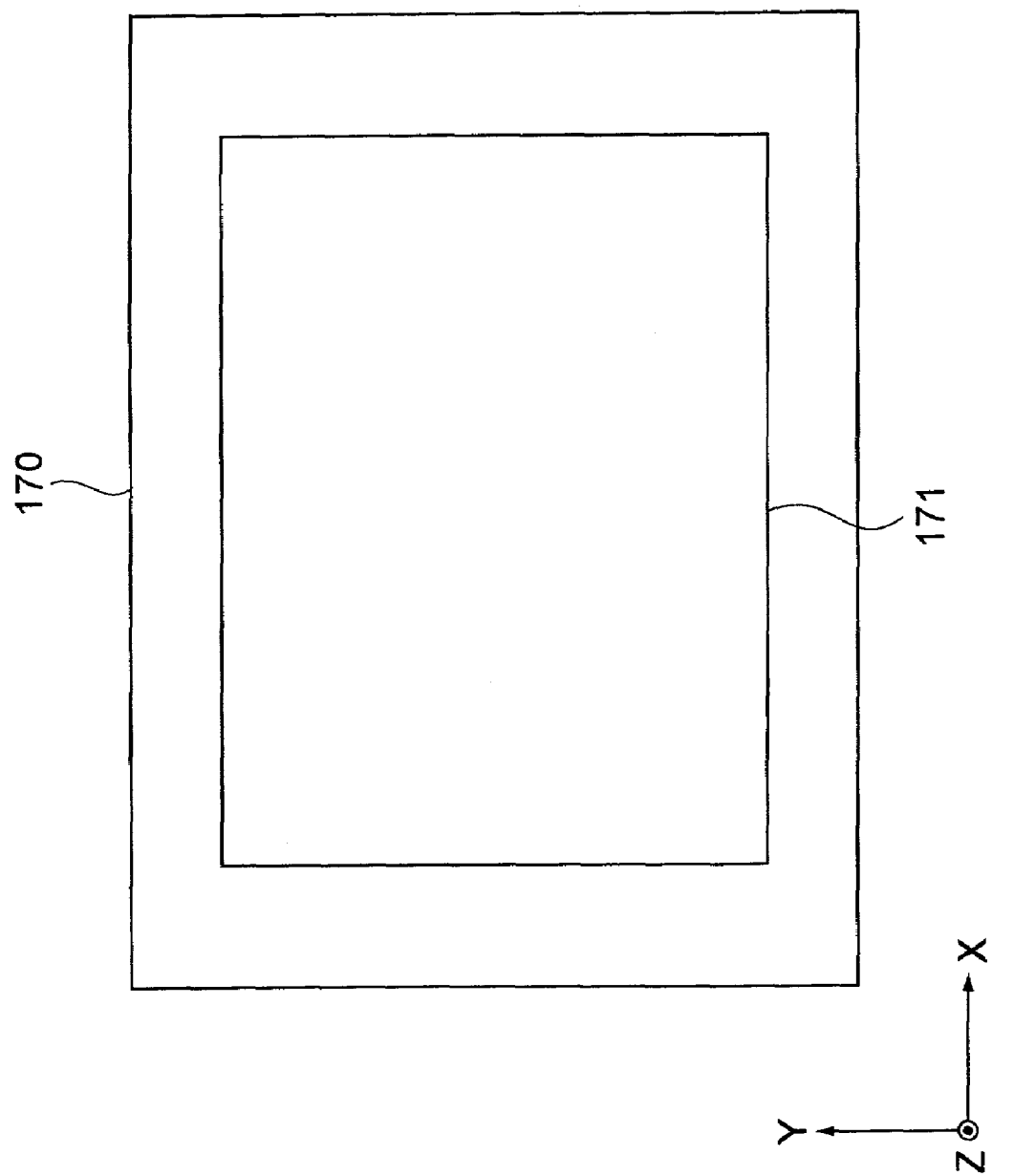
FIG. 6 is a front view showing a projection plate in each embodiment.

As shown in FIG. 6, the ground glass 170 is a predetermined ground glass shaped like a rectangular plate having a parting frame 171 formed like a marking-off on the front surface thereof. An optical image projected onto the front surface is seen through from the rear surface side of the ground glass.

The parting frame 171 is a frame indicating the design illumination region for the optical images superimposed on the liquid crystal panels 141R, 141G, and 141B through the intermediary of the integrator illumination optical system 110 in the foregoing projector 100, and it has a substantially rectangular shape. In other words, the area inside the parting frame 171 will show the optical images actually projected. The superimposing lens 119 is provided with a standard sample that satisfies a predetermined specification, and the standard sample is used for inspections.

The holders 312 through 315 are disposed on a retaining base 316 in the order of the first lens array holder 312, the second lens array holder 313, the superimposing lens holder 314, and the ground glass holder 315, the first lens array holder 312 being the closest to the light source device 320.

Furthermore, the holders 312 through 315 are installed to the retaining base 316 such that the first lens array 113 and the second lens array 115 to be inspected, the superimposing lens 119, and the ground glass 170 oppose each other and their central axes are aligned.

Figure 7:
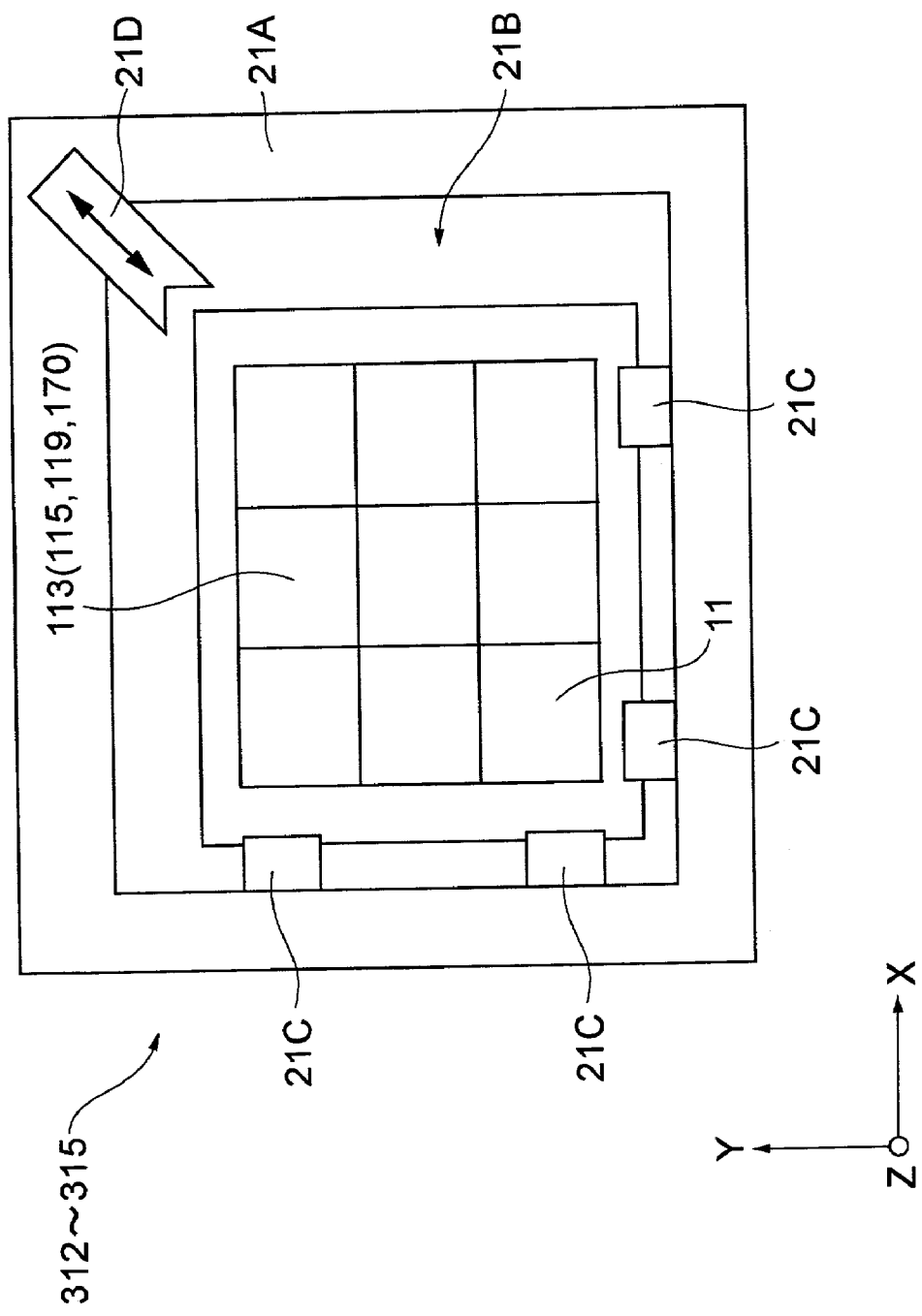
FIG. 7 is a front view showing the structure of a holder in each embodiment.

To be more specific, although the holders 312 through 315 have different sizes, depending upon the objects set thereon, they are provided along the peripheral edge of an opening 21B formed in a frame main body 21A, and are provided with four retaining lugs 21C to retain the first lens array 113, the second lens array 115, the superimposing lens 119, and the ground glass 170, and a movable lug 21D for urging the first lens array 113, the second lens array 115, the superimposing lens 119, and the ground glass 170 in a diagonal direction, as shown in FIG. 7.

Although not shown, elastic members are provided on the portions of the lugs 21C, 21D that abut against the first lens array 113, the second lens array 115, the superimposing lens 119, and the ground glass 170 so as to protect the first lens array 113, the second lens array 115, the superimposing lens 119, and the ground glass 170 from damage.

The movable lug 21D can be moved in the diagonal direction of the first lens array 113, the second lens array 115, the superimposing lens 119, and the ground glass 170 so as to allow the holders 312 through 315 to accommodate different sizes of the first lens array 113, the second lens array 115, the superimposing lens 119, and the ground glass 170.

As shown in FIG. 5, the light source device 320 emits parallel luminous fluxes, and is formed like a box having a substantially T-shaped section with two corner portions of the rectangle cut off. The light source device 320 is equipped with a case 321 with its right end 320R opened, a light source lamp 111A fixedly disposed inside the case 321, and a collimeter lens 112 disposed at the right end 320R of the case 321.

The case 321 has a bottom end portion 320B thereof mounted on a rail 501 that extends in a Z-axis direction on the upper surface of the mounting base 500 so as to be slidable along the rail 501. The case 321 can be fixed at any position along the rail 501.

The position of the case 321 is automatically adjusted before the start of an inspection under the control by the main unit 402, which will be discussed hereinafter, to provide a proper optical distance according to various conditions, including the shapes of the lens arrays 113 and 115.

The light source lamp 111A is a halogen lamp to emit luminous fluxes. The light source lamp 111A for inspection adopts a lamp consuming less energy because detection accuracy can be secured even if the lamp is considerably darker than a product lamp.

The collimeter lens 112 converts the luminous fluxes emitted from the light source lamp 111A into parallel luminous fluxes, and emits the parallel luminous fluxes toward the first lens array 113.

The light source lamp 111A and the collimeter lens 112 are disposed to oppose each other with their central axes aligned.

The image processor 330 is provided with an image detector 331, a display 401, and personal computer 400 having a main unit 402 (FIG. 4).

The image detector 331 is provided with a case 331A shaped like a box having substantially an L-shaped section with one corner of a rectangle cut off and with a left end 330L thereof opened, and an image detector 332 fixedly disposed in the case 331A.

The case 331A has its bottom end portion 330B mounted on a rail 502 that extends in the Z-axis direction on the upper surface of the mounting base 500 so as to be slidable along the rail 502. The case 331A can be fixed at any position along the rail 502.

The position of the case 331A is automatically adjusted before the start of an inspection under the control by the main unit 402, which will be discussed hereinafter, to provide a proper optical distance according to various conditions, including the shape of the superimposing lens 119.

The image detector 332 is constituted by including a CCD (Charge Coupled Device) camera 333 serving as an area sensor and a support base 334 that supports the CCD camera 333 from below and is fixedly disposed on the bottom portion inside the case 331A.

The CCD camera 333 has a CCD 333A (FIG. 8) serving as an image pickup device that splits the parting frame 171 and the optical image projected from the light source device 320 onto the ground glass 170 through the intermediary of the first lens array 113, the second lens array 115, and the superimposing lens 119 into a plurality of pixels to detect them from the rear surface side of the ground glass 170, and converts them into electrical signals, and then outputs the electrical signals to the personal computer 400.

The CCD camera 333 is left secured so as not to be moved during an inspection. However, the CCD camera 333 is provided with a micrometer 335 that permits travel in the Z-axis direction and an adjustment knob 336 that permits circular movement in the Y-axis direction. These micrometer 335 and the adjustment knob 336 are used for the support or the like of the slide of, for example, the image processor 330 along the rail 502, thereby permitting fine adjustment of the position of the CCD camera 333 to be accomplished.

As shown in FIG. 4, the personal computer 400 is a general personal computer equipped with the display 401 and the main unit 402, and electrically connected to the CCD camera 333 by a predetermined connection cable, which is not shown.

The display 401 is a general liquid crystal display, and displays the results of a variety of processing performed by the main unit 402, which will be discussed hereinafter.

The main unit 402 is equipped with a predetermined mother board (not shown) having a CPU, memories, etc. and a capture card (not shown) connected to the mother board so as to be able to perform image processing of the optical images 600 and various types of control by the mother board and the capture card.

Figure 8:
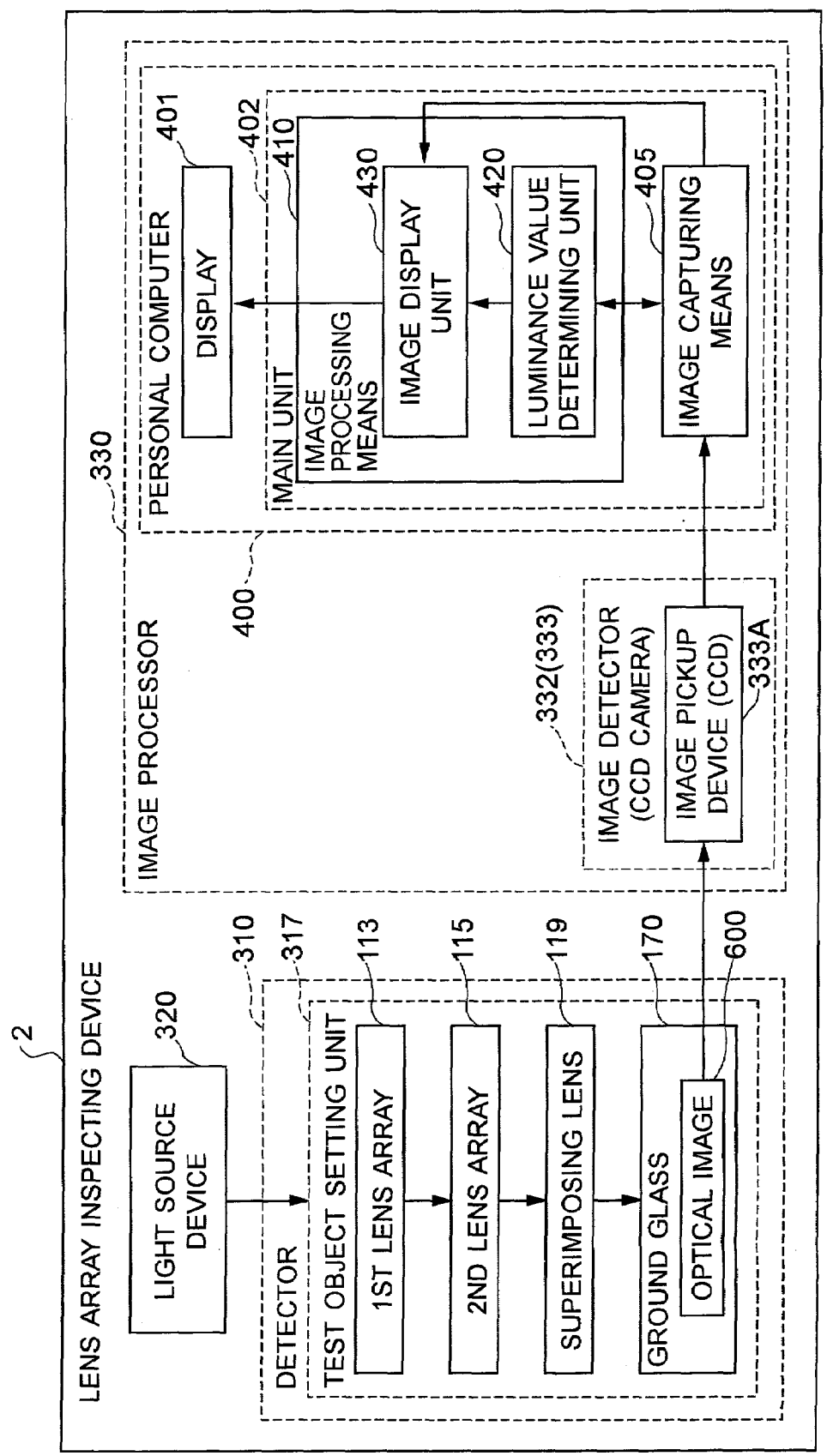
FIG. 8 is a schematic showing the construction of the inspecting device according to a first embodiment.

As shown in FIG. 8, the main unit 402 is constructed by being provided with an image capturing means 405 to capture the electrical signals of the parting frame 171 and the optical images 600 output from the CCD camera 333 as data, and an image processing device 410 to process the captured images.

The image processing means 410 is constructed by being equipped with a luminance value determining unit 420 that compares the captured optical images 600 and the parting frame 171 to determine whether the luminance value of the optical images 600 in the parting frame 171 are not less than a predetermined luminance value, and an image display unit 430 to display determination results, etc. on the display 401. Specific processing procedures will be discussed hereinafter.

<4> Inspection of the Lens Arrays by the Inspecting Device

The inspection of the first lens array 113 and the second lens array 115 by the inspecting device 2 for lens arrays described above is automatically performed by the image detector 332 and the personal computer 400 after diverse types of data associated with the types of projectors with which lens arrays to be inspected are used are registered in advance, and the position of the light source device 320 and the position of the image processor 330 (CCD camera 333) are automatically adjusted. To be more specific, the inspection of the first lens array 113 and the second lens array 115 is performed according to the procedure illustrated in FIG. 9.

<4-1> Registering Data for Each Type of Projector (Processing S1)

This is the processing for registering beforehand the data regarding various types of optical devices associated with the types of projectors and the data indicating required luminance threshold values. Different values are registered according to the types of projectors. In an automated inspection (processing S6) to be discussed hereinafter, the luminance value data for a projector 100 to be inspected is selected from among a plurality of projectors registered by this processing to carry out the automatic inspection.

As specific data, the sizes of the image forming regions of the liquid crystal panels 141R, 141G, and 141B, and the luminance threshold value data for each type are registered.

The data for each type of projector thus created is saved in a text file, and used in the main unit 402 of the personal computer 400, as necessary.

<4-2> Installing the Test Object Setting Unit (Processing S2)

A test object setting unit 317 associated with the projector 100 is prepared, the first lens array 113 to be inspected is set on the first lens array holder 312, and the second lens array 115, the superimposing lens 119, and the ground glass 170 that are the standard samples satisfying predetermined requirements are set on the associated remaining holders 313, 314, and 315, respectively.

Subsequently, the handle 300A is held and the cover 310T is circularly moved to open the upper end of the case 311, then the test object setting unit 317 is installed at a predetermined position in the case 311. Thereafter, the cover 310T is circularly moved to set it back to close the upper end of the case 311. Closing the cover 310T prevents light from leaking out of the case 311 and external disturbance light from affecting the case 311.

<4-3> Adjusting the Positions of the Light Source Device and the Image Detector

The type data associated with the combination of the present illumination optical devices 113, 115, 119, and 170 is called up (Processing S3) from among the data regarding the type of the projector 100 that has been registered in the processing S1. Based on the called-up type data, the position of the light source device 320 is adjusted such that the distance thereof conforms to a design optical distance, and the position of the image detector 331 including the CCD camera 333 is adjusted such that the parting frame 171 of the ground glass 170 is centered (Processing S4). At this time, the luminance threshold value based on the selected type data is read onto a memory of the main unit 402.

<4-4> Specifying the Number of Scanning Lines for Inspection (Processing S5)

Figure 13:
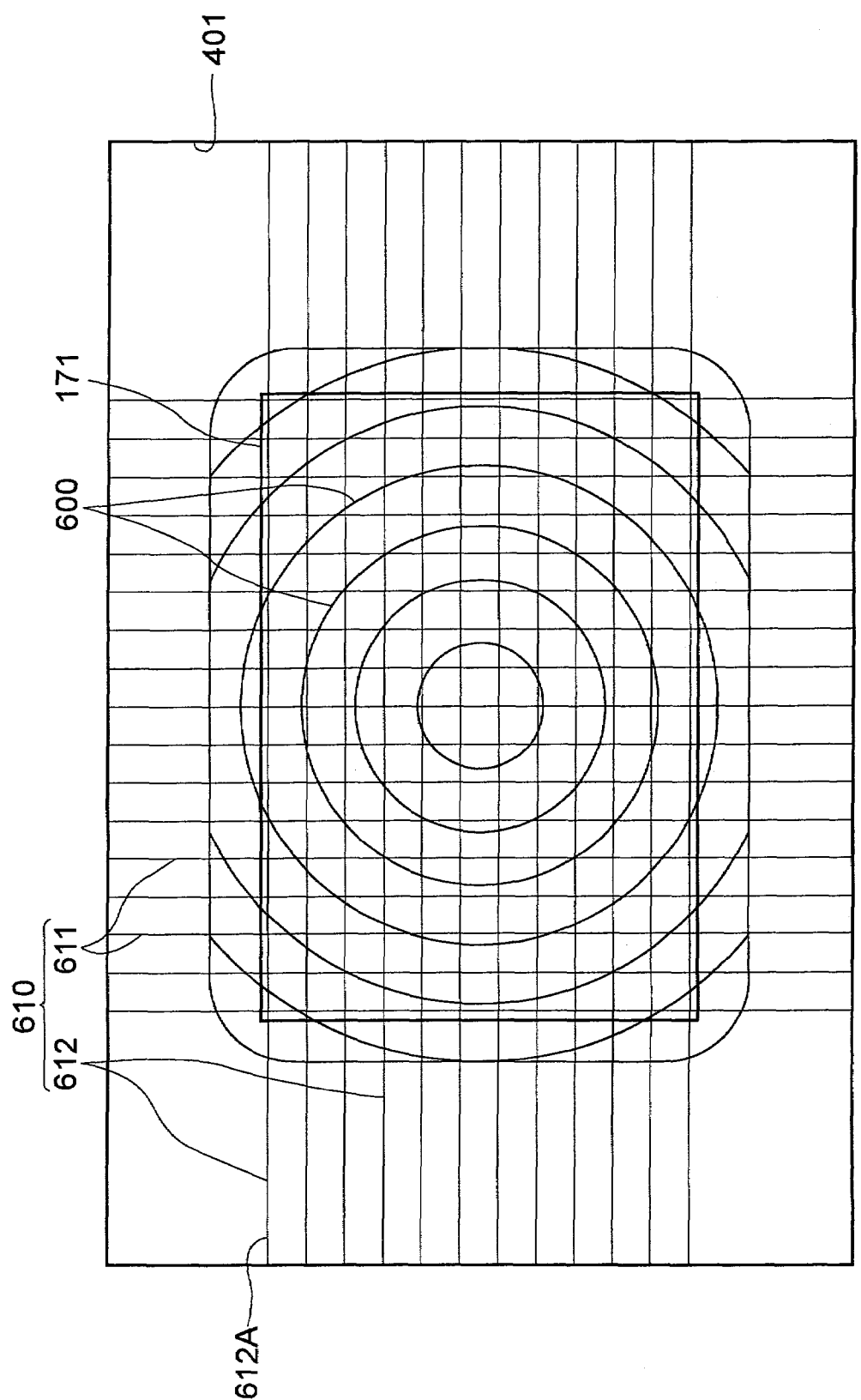
FIG. 13 is a schematic showing the detail displayed on the display screen of the inspecting device in each embodiment mentioned above.

Next, the number of scanning lines 610 (FIG. 13) to inspect the optical images 600 detected as a plurality of pixels is specified. The scanning lines 610 are sets of pixels arranged in predetermined directions. In FIG. 13, vertical scanning lines 611 formed of pixels vertically arranged and the horizontal scanning lines 612 formed of pixels horizontally arranged are shown in solid lines.

Increasing the number of such scanning lines 610 increases the number of pixels inspected, thus permitting the inspection to be accomplished with higher accuracy. On the other hand, decreasing the number of the scanning lines 610 decreases the number of pixels inspected, so that the inspection can be finished in a shorter time. This means that the number of the scanning lines may be arbitrarily set according to a test object.

<4-5> Automatic Inspection (Processing S6)

Figure 10:
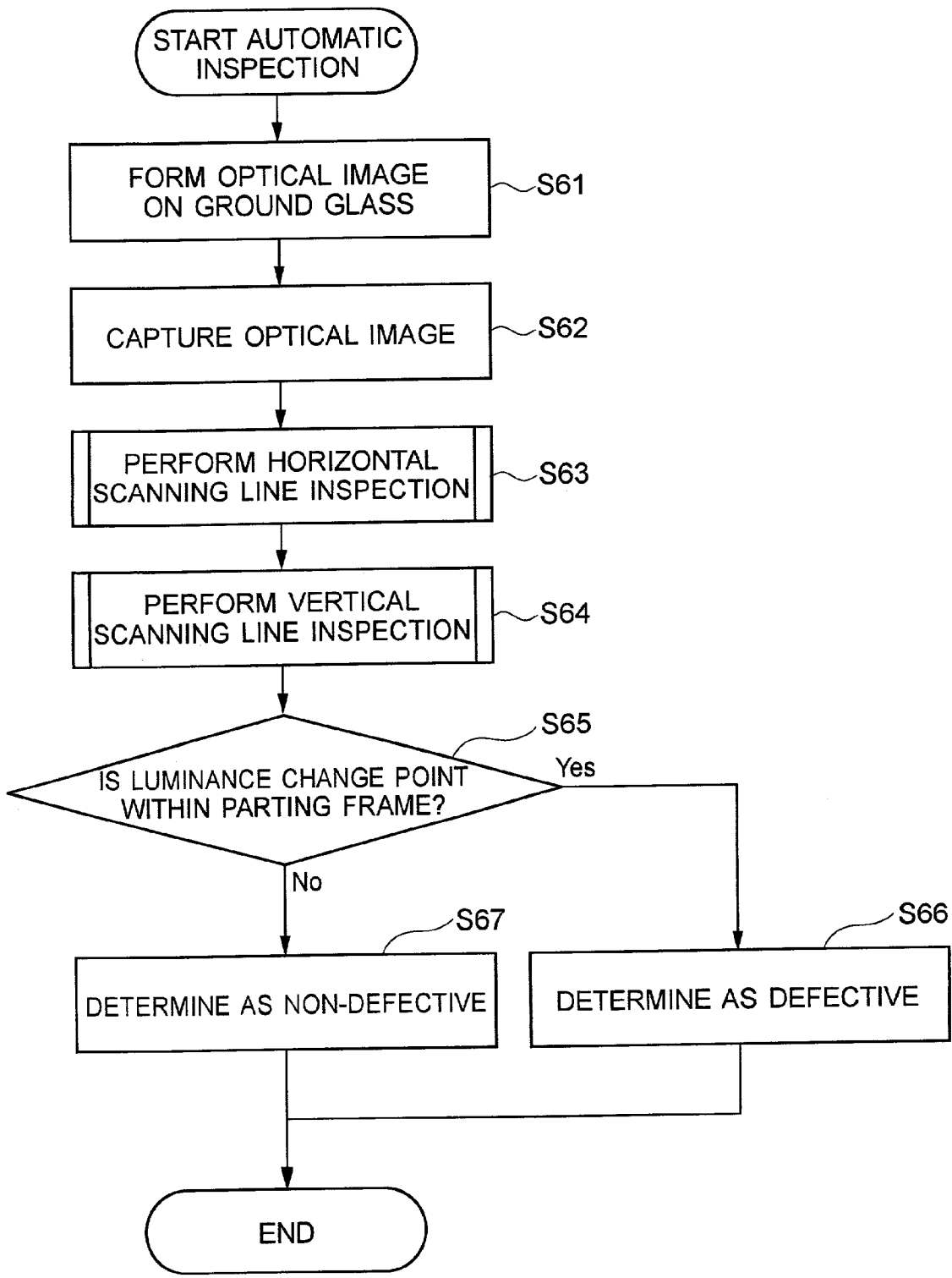
FIG. 10 is a flowchart illustrating an inspection procedure performed by the inspecting device according to the first embodiment.

After completing the aforesaid setting, clicking START INSPECTION button 700 (FIG. 16) automatically begins the inspection. The automatic inspection is performed according to the flow charts shown in FIG. 10 and FIG. 11.

<4-5-1> Forming Optical Images (Processing S61: Procedure for Forming Optical Images)

Figure 12:
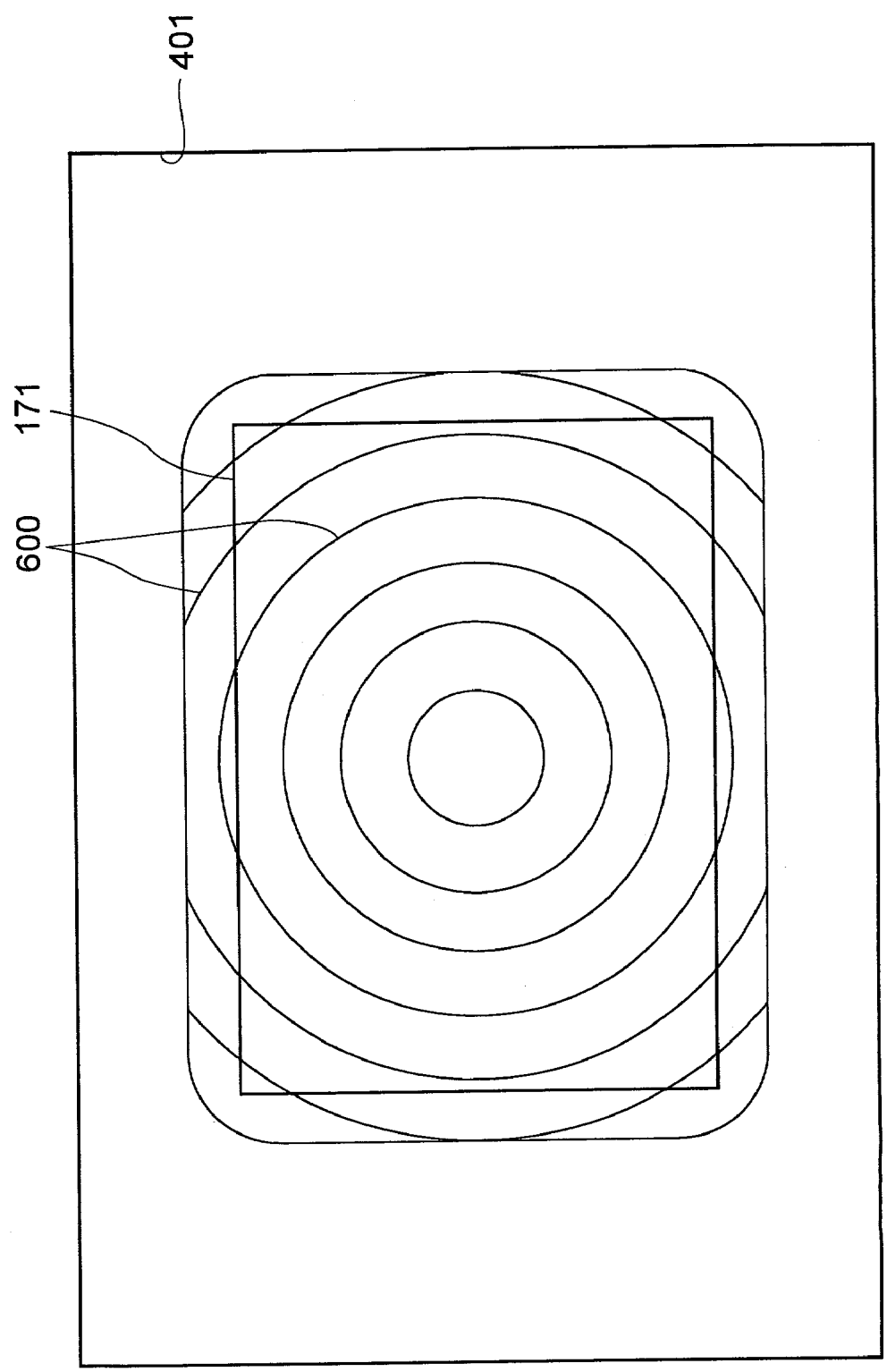
FIG. 12 is a schematic showing the detail displayed on the display screen of the inspecting device in each embodiment mentioned above.

A parallel luminous flux emitted from the light source device 320 passes through the lens arrays 113 and 115 and the superimposing lens 119, and is projected onto the ground glass 170 to form the optical images 600 (FIG. 12).

<4-5-2> Capturing Optical Images (Processing S62: Procedure for Capturing Images)

The projected optical images 600 are picked up by the CCD camera 333, converted into signals suited to a computer by the image capturing device 405, and the signals are output to the image processing means 410.

Based on the signals, the image display unit 430 causes the optical images 600 and the parting frame 171 to be displayed on the display 401 (FIG. 12). The luminance of the optical images 600 is such that it is the highest in a portion corresponding to the central axis thereof and it decreases as the distance from the center increases. In other words, as schematically illustrated in FIG. 12, the detected optical images 600 gradually darken outward.

<4-5-3> Inspection Using Scanning Lines (a) Horizontal Scanning Line Inspection (Processing S63)

Figure 11:
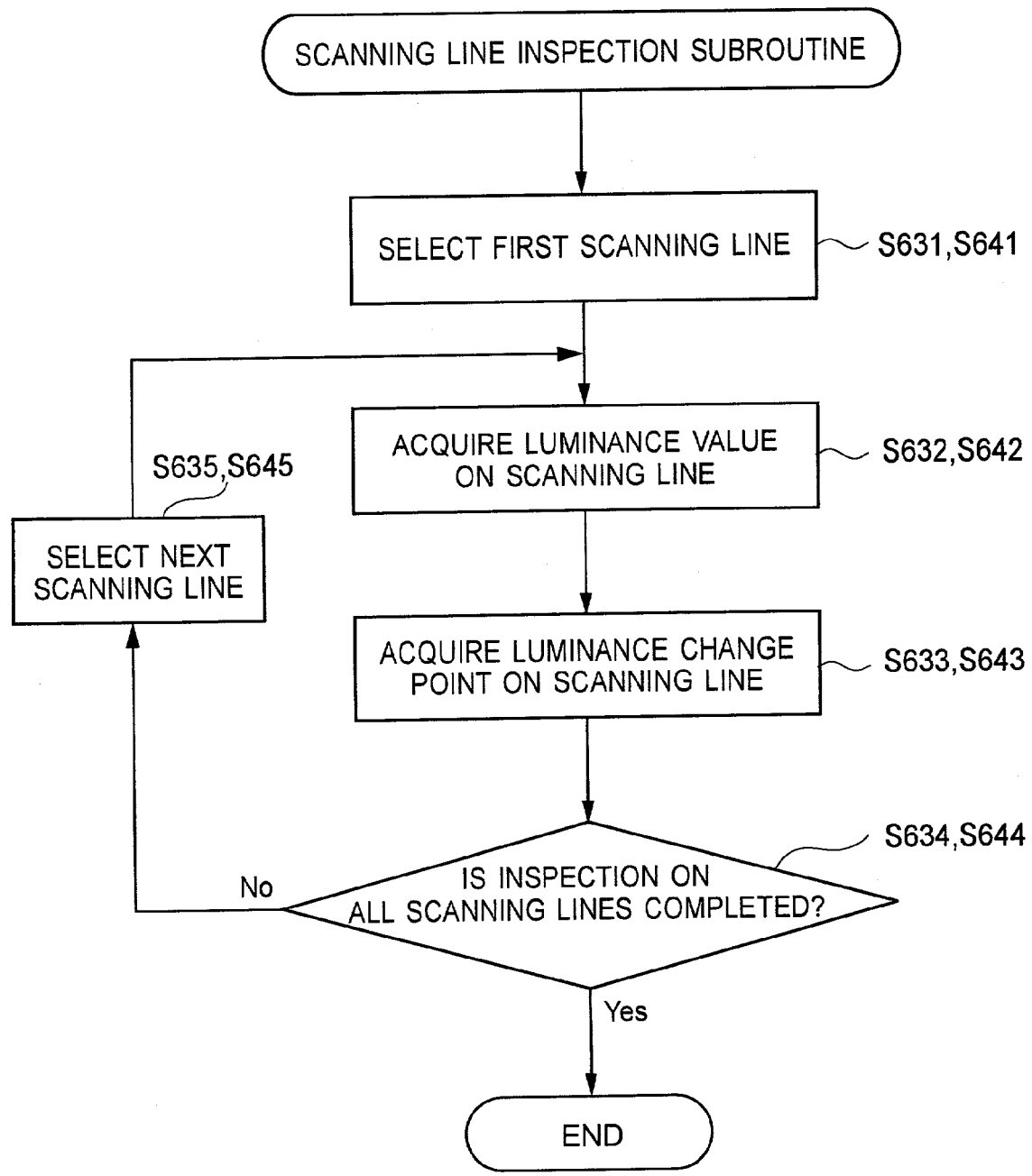
FIG. 11 is a flowchart illustrating an inspection procedure performed by the inspecting device in each embodiment mentioned above.

As shown in FIG. 11 and FIG. 13, based on the image data captured by the image capturing device 405, the image processing means 410 selects an uppermost horizontal scanning line 612A from among the horizontal scanning lines 612 (Processing S631), and acquires the luminance value of each pixel on the selected horizontal scanning line 612A (Processing S632: Procedure for acquiring luminance values).

The luminance value determining unit 420 compares the luminance values acquired on the respective pixels on the horizontal scanning line 612A with a registered threshold value that has been registered in advance. Then, the range of the pixels having the predetermined threshold value or more are detected among the pixels on the horizontal scanning line 612A so as to detect a luminance change point indicating the position of the boundary between the pixels having the luminance of the threshold value or more and the pixels having luminance below the threshold value (Processing S633: Luminance change position acquiring step).

The image display unit 430 causes a mark "+" to be displayed at a luminance change position on the display 401. For instance, on the horizontal scanning line 612A, marks "+" 602 and 603 in FIG. 14 indicate the luminance change points.

Next, the image processing device 410 determines whether the luminance detection on all the horizontal scanning lines 612 has completed (Processing S634: Scanning line inspection determining step).

If it is determined that the inspection of all the horizontal scanning lines 612 is completed, then the image processing means 410 terminates (processing S63), and proceeds to (processing S64), which is the subsequent processing. On the other hand, if it is determined that the inspection on all the horizontal scanning lines 612 has not yet completed, then the image processing means 410 selects the following horizontal scanning line 612 (processing S635), proceeds to the foregoing (processing S632), and inspects up to the last horizontal scanning line 612Z in FIG. 14.

The inspection on the horizontal scanning lines is performed as described above.

(b) Vertical Scanning Line Inspection (Processing S64)

The vertical scanning line inspection is substantially the same as the horizontal scanning line inspection described above, and it is performed according to the procedure illustrated in FIG. 11. The only difference is whether the direction of the inspection is horizontal or vertical.

Figure 14:
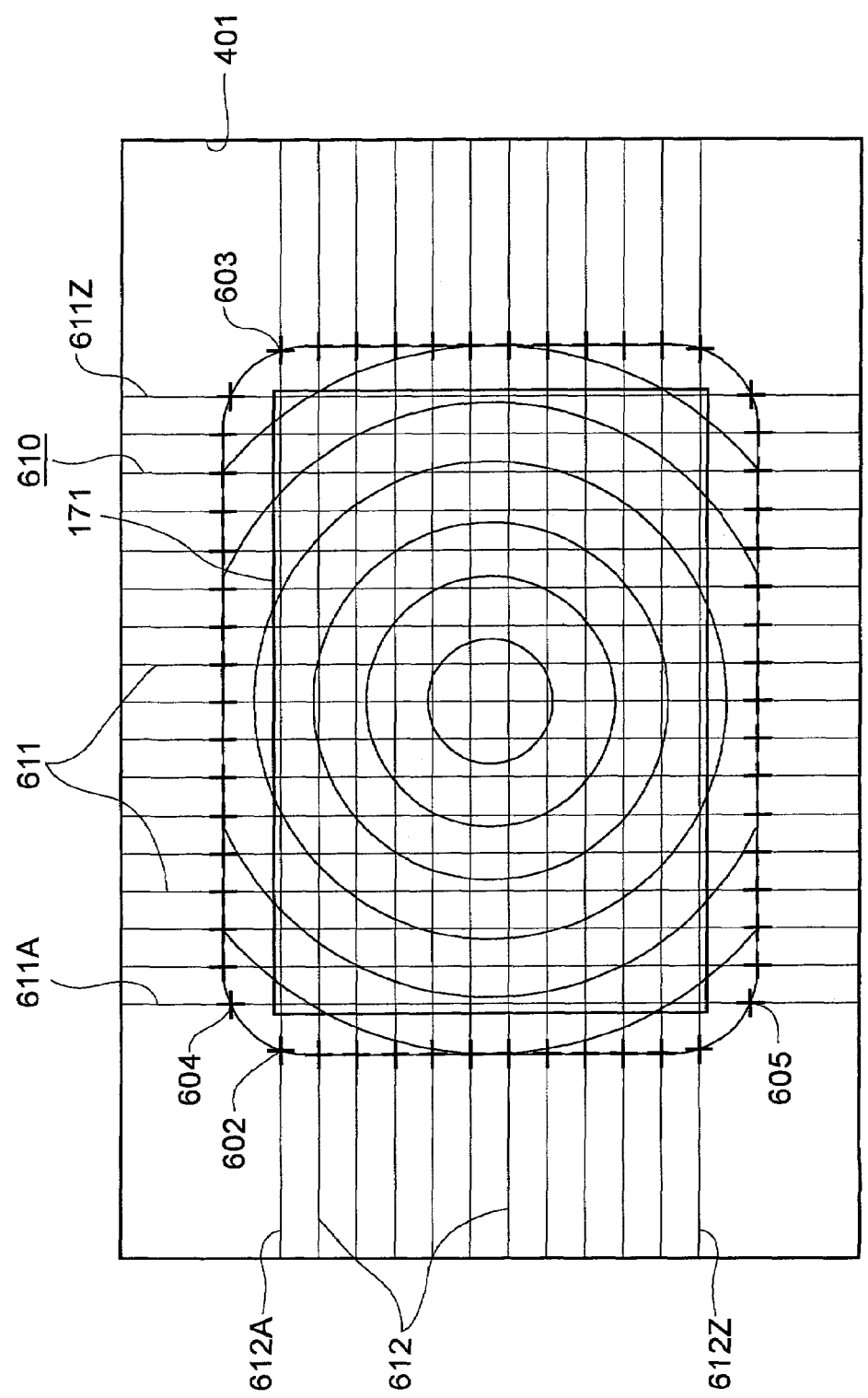
FIG. 14 is a schematic showing the detail displayed on the display screen of the inspecting device in each embodiment mentioned above.

To be more specific, in FIG. 14, a leftmost vertical scanning line 611A is selected from among the vertical scanning lines 611 (processing S641), and the luminance value of each pixel on the selected vertical scanning line 611A is acquired processing S642) so as to detect luminance change points on the vertical scanning line 611A (processing S643). This detection is performed in the same manner from the leftmost vertical scanning line 611A to a rightmost vertical scanning line 611Z (processing S644). The specific procedure is the same as that described above, and it will be omitted.

<4-5-4> Determining the Position of a Luminance Change Point

Upon completion of the inspection of all the scanning lines 610 as discussed above, the luminance value determining unit 420 determines whether these marks "+" indicating the luminance change points are within the range inside the parting frame 171 (Processing S65: Step for determining luminance change positions).

More specifically, if it is determined that there is a portion of an insufficient luminance in the parting frame 171 requiring a predetermined luminance, then it indicates that the first lens array 113, which is a test object, is defective (processing S66), or if it is determined that there is no portion of an insufficient luminance, then it indicates that the first lens array 113, which is the test object, is non-defective (processing S67).

Figure 16:
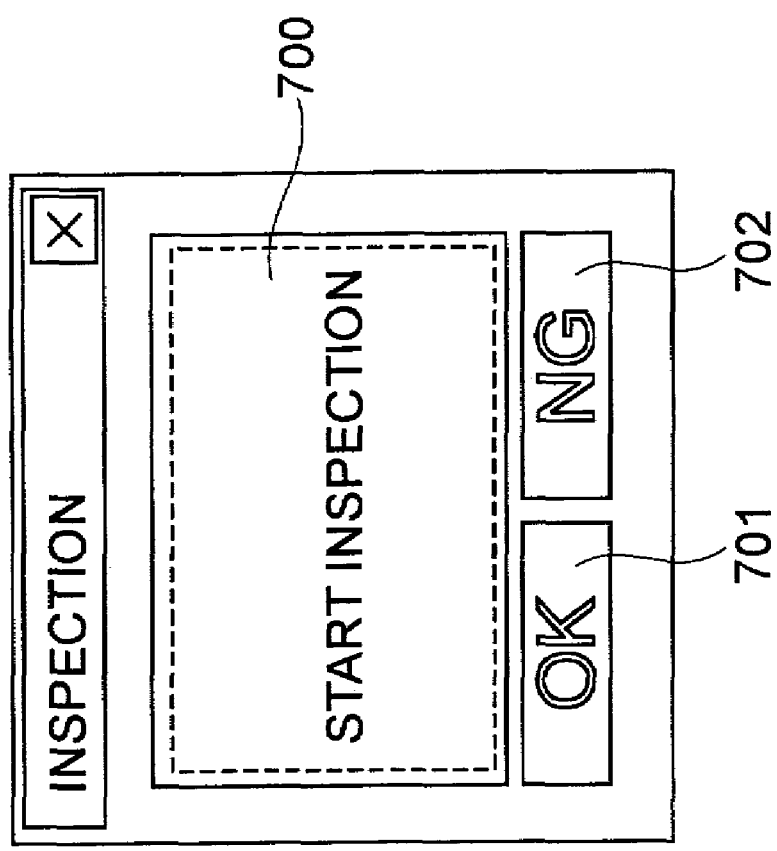
FIG. 16 is a schematic showing the detail displayed on the display screen of the inspecting device in each embodiment mentioned above.

If the luminance value determining unit 420 determines that there is no mark "+" indicating a luminance change point in the area inside the parting frame 171, as shown in FIG. 14, then the image display unit 430 displays "OK 701" on the display 401 to indicate that the first lens array 113, which is the test object, is non-defective, as shown in FIG. 16.

Figure 15:
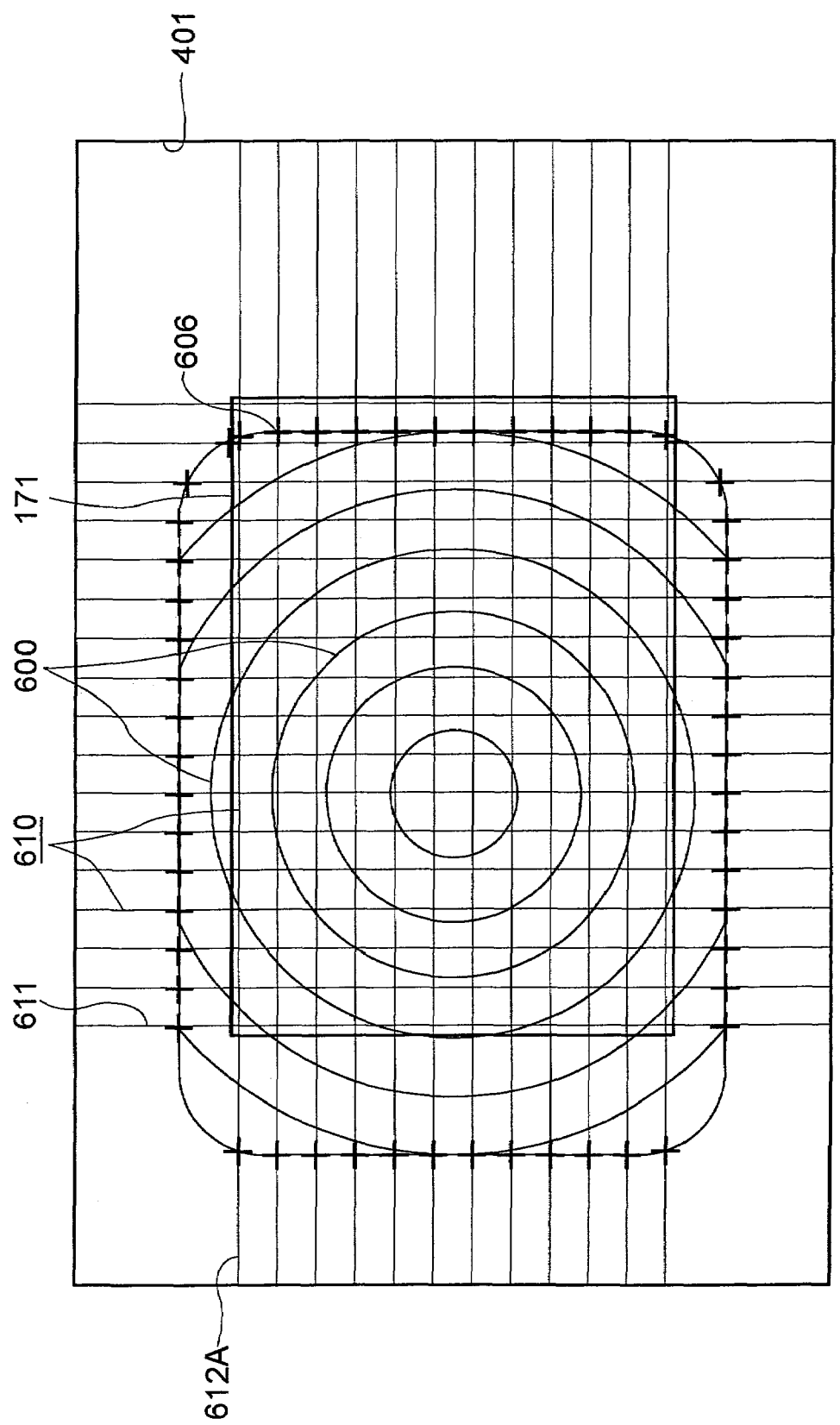
FIG. 15 is a schematic showing the detail displayed on the display screen of the inspecting device in each embodiment mentioned above.

On the other hand, if the luminance value determining unit 420 determines that there are the marks "+" indicating luminance change points in the area inside the parting frame 171, as shown in FIG. 15, (e.g., a mark "+" 606 in FIG. 15), then the image display unit 430 displays "NG 702" on the display 401, as shown in FIG. 16, to indicate that the first lens array 113, which is a test object, is defective.

If the area of the marks "+" indicating luminance change points is considerably shifted with respect to the parting frame 171, resulting in NG determination, then the shift amount is calculated and the amount of shift required to make the test object non-defective is displayed. In addition, it is determined if the value is not more than a specified value and the determination result is displayed. This saves the lenses that can be adjusted in an optical axis adjustment step, permitting reduced cost to be achieved.

<4-6> Storing Inspection Data (Processing S7)

Upon completion of the aforesaid automatic inspection, the obtained inspection data and inspection results are stored as a predetermined data file in a memory or the like of the main unit 402, as necessary. The stored inspection data or the like can be displayed in the form of a list or output by a printer, as necessary.

<5> Effects of the Embodiment

According to the present embodiment discussed above, the following effects will be obtained.

(1) Since the parting frame 171 suited to an illumination region is formed, if any portion darker than a design luminance is detected in the parting frame 171, then it can be determined that the first lens array 113 is defective, permitting easy inspection of the optical characteristics of the first lens array 113. Thus, the optical characteristics of the first lens array 113 can be inspected simply by setting the first lens array 113 on the first lens array holder 312. This obviates the need to inspect the first lens array 113 after assembling all the components into a projector with considerable effort, as in the past, so that the load of the inspecting operation can be reduced, and the manufacturing cost can be controlled.

(2) The light source device 320 is provided, so that a constant luminous flux is always emitted from the light source device 320, obviating the need to consider errors caused by the light source device 320. Hence, the first lens array 113 as a test object can be inspected with higher accuracy.

(3) A plurality of test object setting units are prepared according to the types of the projector 100. The sizes, dispositions, etc. of illumination optical devices, such as the lens arrays 113 and 115 and the ground glass 170, differ according to the type of a projector to be used. The above arrangement obviates the need for cumbersome readjustment of the dispositions or the like of the illumination optical devices each time the type of the projector changes, so that a test object can be easily disposed, permitting a further reduced load of the inspecting operation.

(4) The provision of the image capturing device 405 to capture the optical images 600 detected by the CCD 333A and the image processing device to process the optical images 600 makes it possible to automatically measure the luminance values of the optical images 600. This arrangement allows pass/fail to be easily determined simply by comparing the detected parting frame 171 with the processed optical images 600, thus permitting a reduced load of the inspecting operation.

(5) The provision of the luminance value determining unit 420 makes it possible to automatically determine whether the luminance values of the optical images 600 in the parting frame 171 are not less than a predetermined luminance value, thus permitting a reduced load of the inspecting operation.

(6) The light source device 320 is constructed so as to be movable forward/backward with respect to an illumination optical axis of a parallel luminous flux to be emitted. Hence, even when the shapes, sizes, etc. of the illumination optical devices, such as the first lens array 113 and the second lens array 115, change, the optical distance can be easily adjusted by moving the light source device 320 forward or backward in the direction of an illumination optical axis according to such changes, permitting compatibility with a plurality of types of illumination optical devices.

(7) The test objects are the lens arrays 113 and 115, which are luminous flux splitting devices. Considering that the lens arrays 113 and 115 have particularly poor yields among illumination optical devices, the yield of the projector 100 as a finished product can be improved simply by inspecting the lens arrays 113 and 115, and efficient inspection can be achieved.

(8) Inspection results and the optical images 600 are shown on the display 401, so that the first lens array 113 can be easily inspected by visually check on the display 401.

(9) The number of the scanning lines 610 can be selected, so that the number can be changed according to a test object, thus allowing inspection accuracy and inspection time to be adjusted.

(10) The inspection can be performed simply by registering a variety of types of data associated with the types of projectors in advance. Hence, even if, for example, new types are added, this can be easily dealt with merely by entering the data corresponding to the added types. At this time, the test object setting units 317 compatible with the added types may be prepared.

Second Embodiment

A lens array inspecting device 3 according to a second embodiment of the present invention will now be explained. The lens array inspecting device 3 according to the second embodiment and the lens array inspecting device 2 according to the first embodiment differ in the automatic inspection method, namely, the method to determine pass/fail of the first lens array 113. Thus, an image processing device 410 is provided with a program that updates its configuration according to a change of the pass/fail determining method. The rest of the construction is the same as the construction of the first embodiment, and like or equivalent components as those of the first embodiment will be assigned like reference numerals and the explanation thereof will be omitted or simplified.

Figure 17:
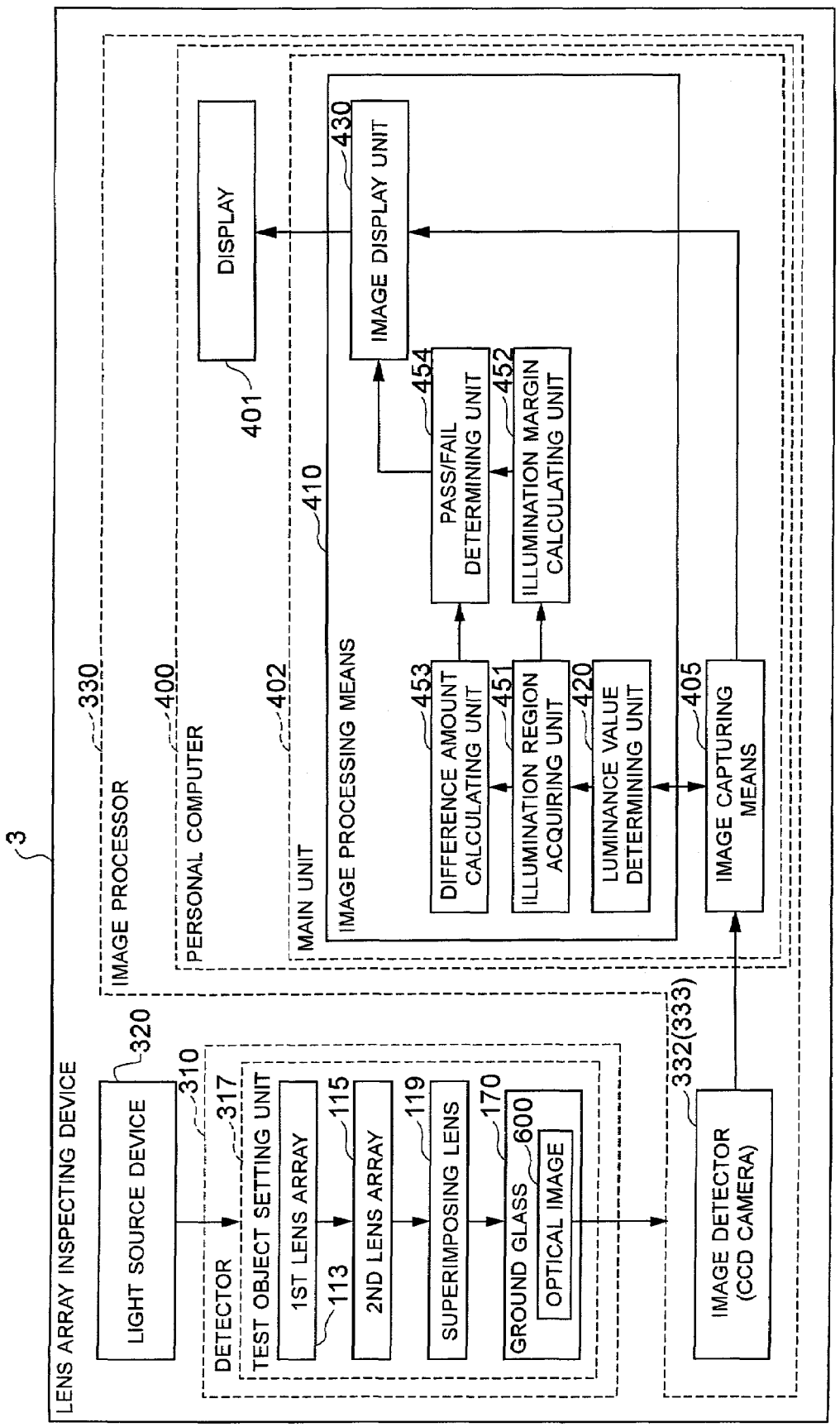
FIG. 17 is a schematic showing the construction of the inspecting device in the above embodiment.
Figure 20:
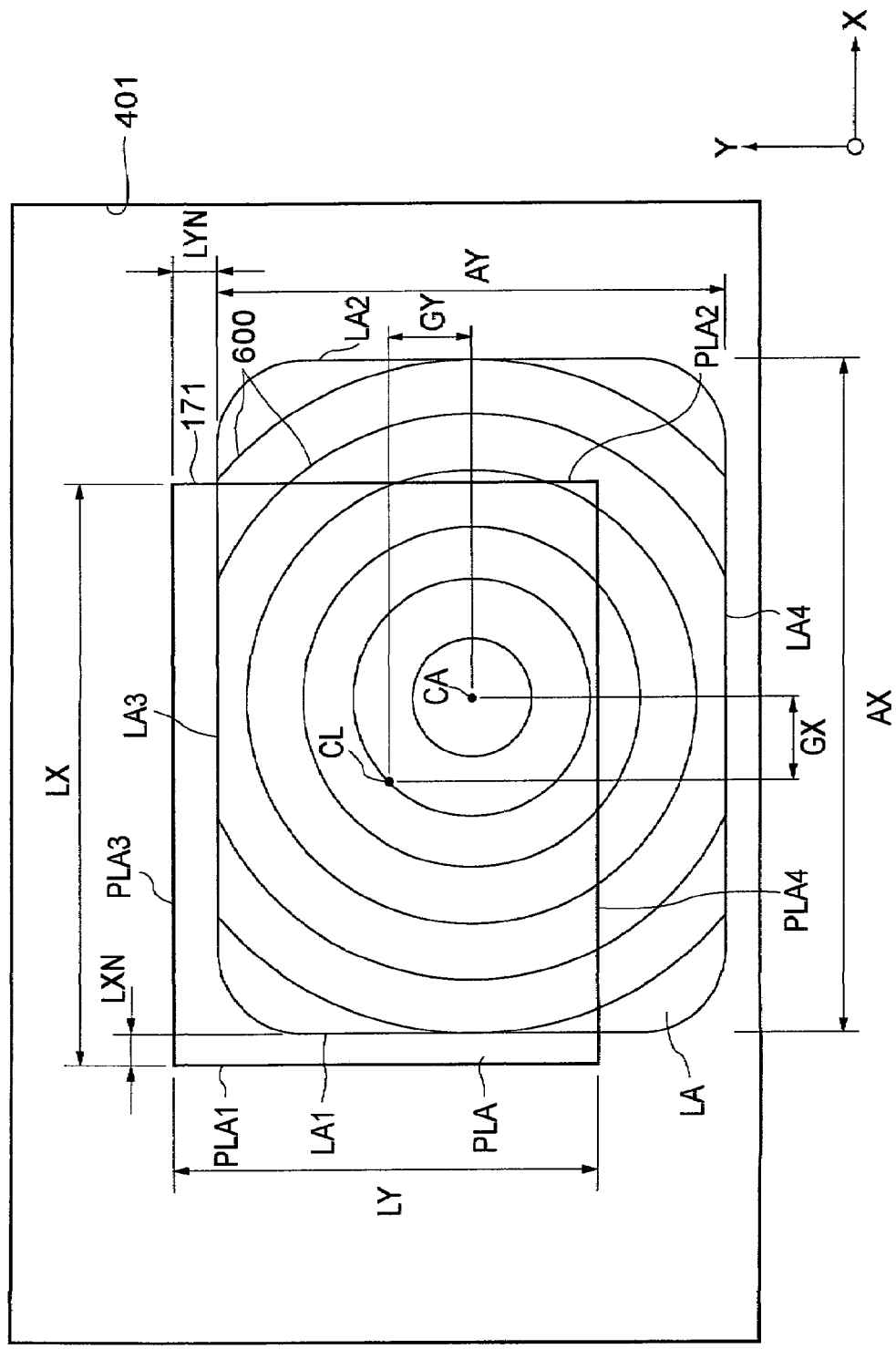
FIG. 20 is a schematic showing an illuminated region and an illumination region in the second embodiment.

The image processing device 410 constituting the main unit 402 is equipped with the luminance determining unit 420 and the image display unit 430, as shown in FIG. 17. Referring also to FIG. 20, the image processing device 410 is further equipped with an illumination region acquiring unit 451 to acquire a region in which the luminance value is not less than a preset luminance threshold value in optical images 600 as an illumination region LA, an illumination margin calculating unit 452 that calculates an illumination margin from an illuminated region PLA defined by the illumination region LA and the parting frame 171, a difference amount calculating unit 453 that calculates the amount of central difference between centers CA and CL thereof on the basis of the center CA of the illumination region LA and the center CL of the illuminated region PLA, and a pass/fail determining unit 454 that determines whether the first lens array 113 is non-defective or defective on the basis of the illumination margin and the central difference amount. Specific processing procedures will be discussed hereinafter.

<6> Inspecting Lens Arrays by the Inspecting Device

Figure 9:
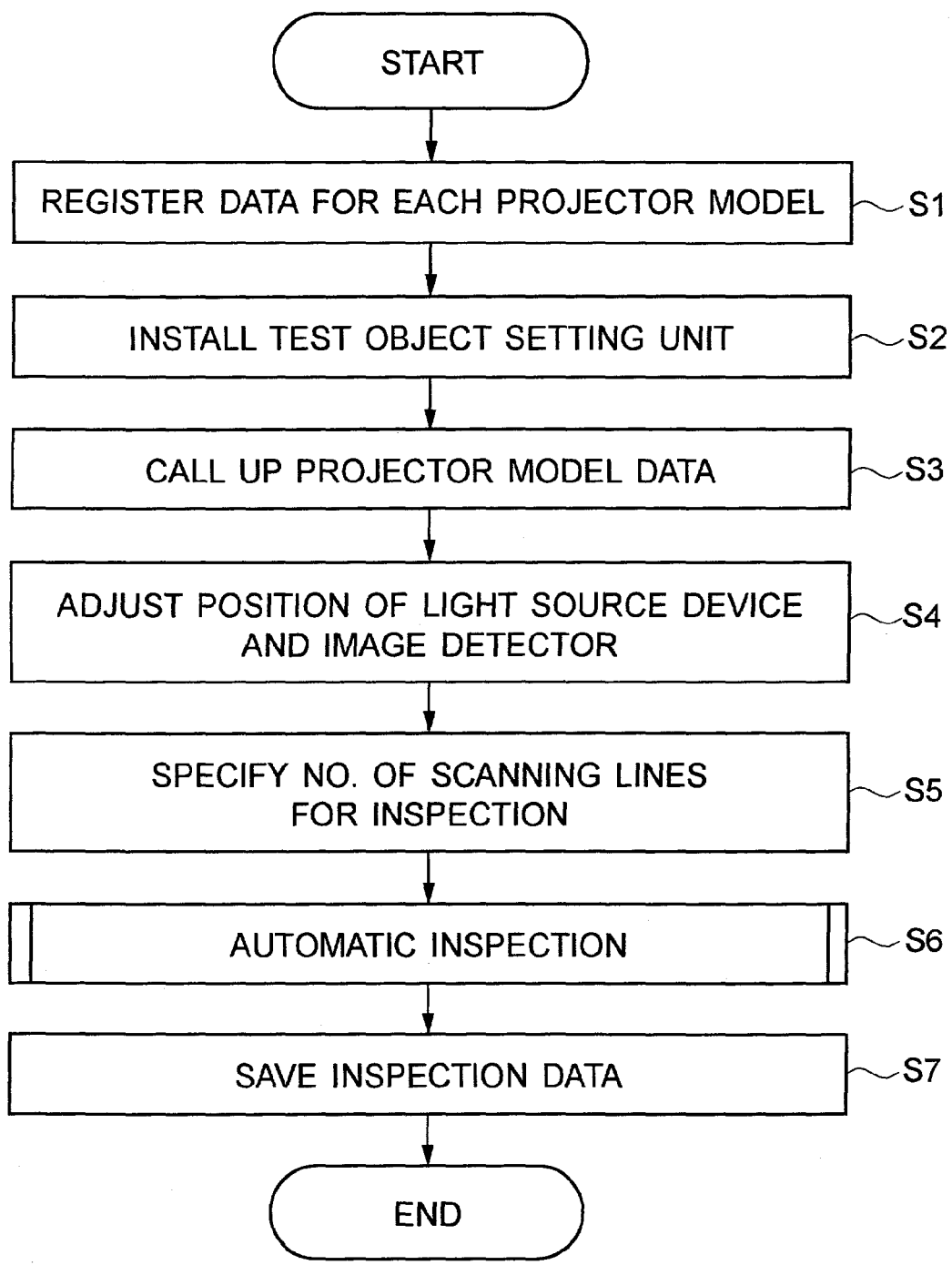
FIG. 9 is a flowchart illustrating an inspection procedure performed by the inspecting device in each embodiment mentioned above.
Figure 18:
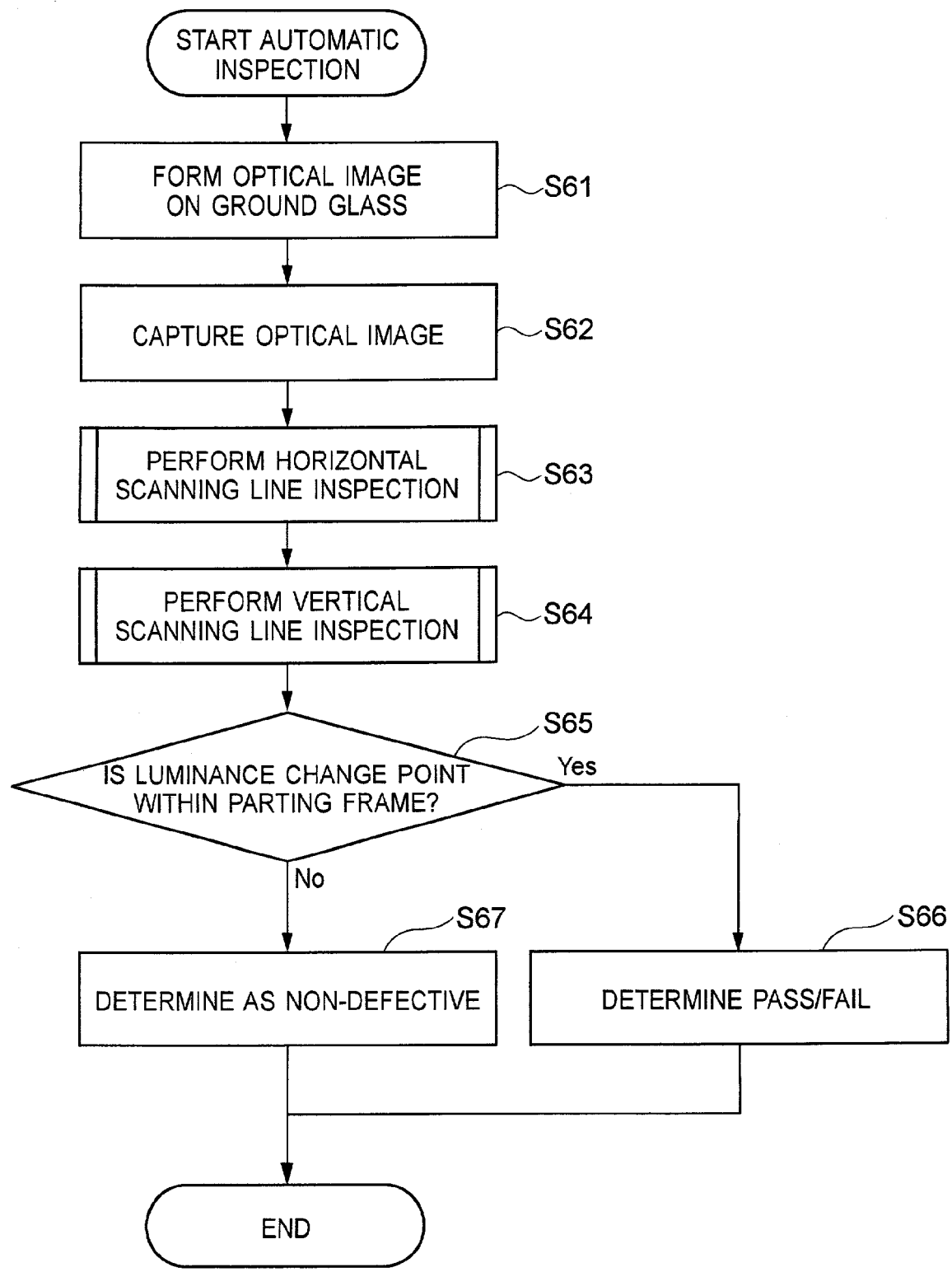
FIG. 18 is a flowchart illustrating the procedure for an automatic inspection in the second embodiment.

In the lens array inspecting device 3, the inspection of the first lens array 113 is carried out according to the procedures shown in FIG. 9 and FIG. 18. The procedure shown in FIG. 9 is the same as that for the first embodiment, so that the explanation thereof will be omitted. In FIG. 18, processing of S61 through processing of S67 are substantially the same as those shown in FIG. 10 in the first embodiment. However, the processing 66 in the first embodiment determines merely "defective", while the processing 66 in this embodiment determines whether the first lens arrays 113 determined "defective" in the first embodiment have been determined "defective" merely because of misaligned setting of the first lens arrays 113 to determine pass/fail of the first lens arrays 113 according to the procedure shown in FIG. 19.

Figure 19:
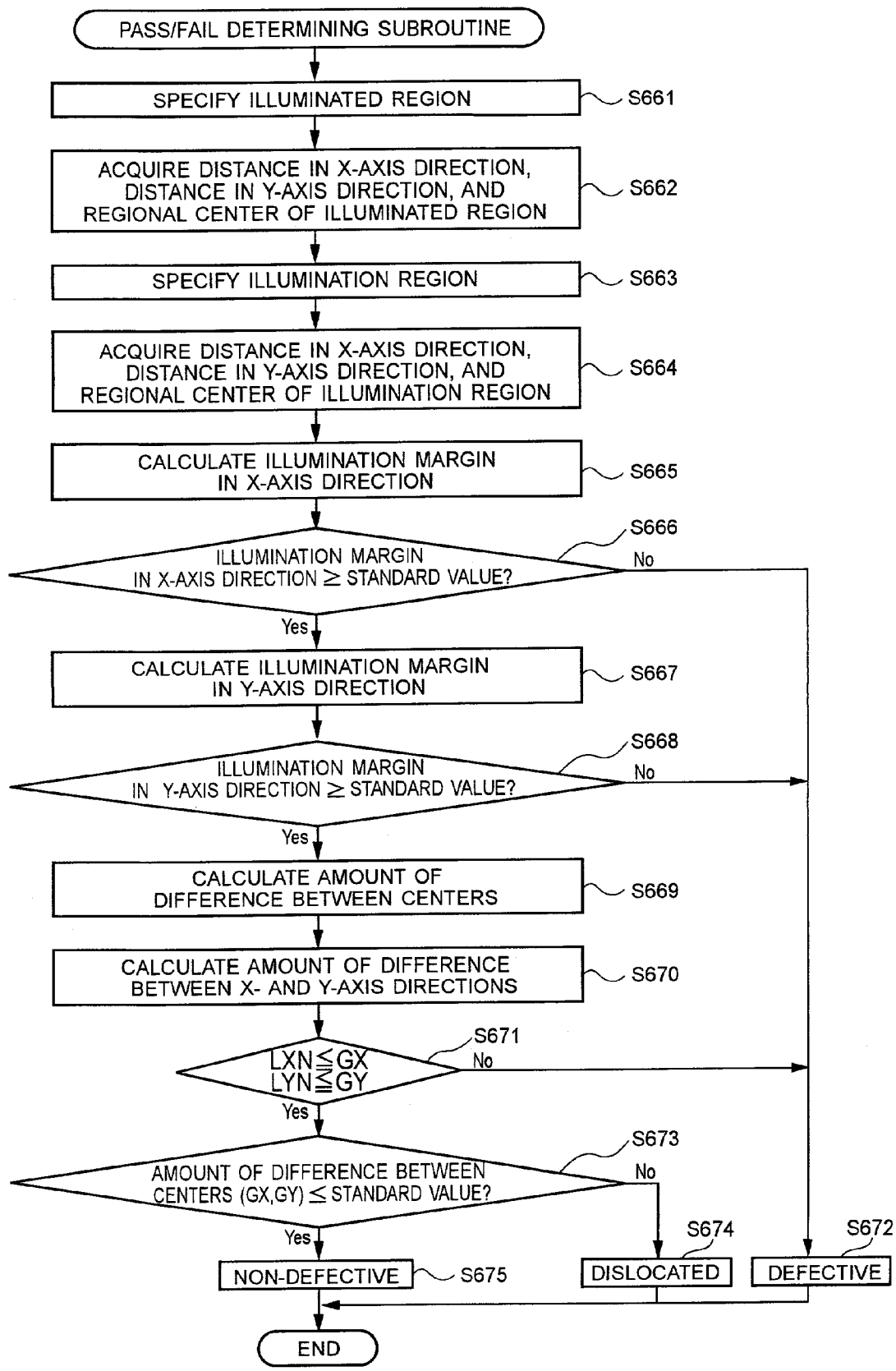
FIG. 19 is a flowchart illustrating the procedure for determining pass/fail in the second embodiment.

Referring now to FIGS. 17 and 20 in conjunction with the flow chart of FIG. 19, the procedure to determine pass/fail (processing S66) will be explained.

FIG. 20 is a schematic showing the parallel luminous flux emitted from the light source device 320 passes through the lens arrays 113 and 115 and the superimposing lens 119, and an optical image 600 projected onto the ground glass 170, on which the parting frame 171 is formed, is displayed on the display 401.

As shown in FIG. 20, in the plane of the ground glass 170 that is orthogonal to the illumination optical axis of the parallel luminous flux, an orthogonal coordinate system formed of an X-axis and a Y-axis is set along the two sides of the rectangular parting frame 171 that are orthogonal to each other.

To inspect the first lens array 113, the illuminated region PLA defined by the parting frame 171 is first specified (processing S661). Then, in the specified illuminated region PLA, a distance LX in an X-axis direction of the illuminated region PLA, which is the length in the X-axis direction, a distance LY in a Y-axis direction of the illuminated region PLA, which is the length in the Y-axis direction, and a center CL of the illuminated region, which is the center of the illuminated region PLA are acquired (processing S662).

To be more specific, as shown in FIG. 20, first, in the rectangular illuminated region PLA, the XY coordinates of all pixels constituting four sides PLA1 through PLA4 that provide the end portions thereof are determined. Then, on the two sides PLA1 and PLA2 that are parallel in the Y-axis direction, average X coordinates showing average X coordinates of the pixels on the sides PLA1 and PLA2 are respectively determined. Likewise, on the two sides PLA3 and PLA4 that are parallel in the X-axis direction, average Y coordinates showing average Y coordinates of the pixels on the sides PLA3 and PLA4 are respectively determined.

The average X coordinates and the average Y coordinates may alternatively be determined on the basis of the design position coordinate data for each type of projector that has been stored in the main unit 402 of the personal computer 400 in advance. In this case, the data may be called up from a storage or the like (not shown) of the main unit 402.

Subsequently, the distance LX in the X-axis direction and the distance LY in the Y-axis direction of the illuminated region PLA are determined on the basis of the average X coordinates of the opposing two sides PLA1 and PLA2 or the average Y coordinates of the opposing two sides PLA3 and PLA4. Furthermore, the center CL of the illuminated region, which is a central XY coordinate of the illuminated region PLA, is acquired on the basis of the XY coordinates or the like of four apexes in the rectangular illuminated region PLA.

Next, the region wherein the luminance value is not less than a preset luminance threshold value, that is, a substantially rectangular illumination region LA surrounded by the marks "+" 602 and 603 (refer to FIG. 14) that indicate the foregoing luminance change points is specified by the illumination region acquiring unit 451 (Processing S663: Procedure to acquire an illumination region). The illumination region LA is specified by the XY coordinate of each constituent pixel.

In specifying the illumination region LA, there are cases where the positions of the sides LA1 through LA4 providing the end portions of the rectangular illumination region LA change with consequent variations in the XY coordinates of the end portions, depending on the image pickup timing of the CCD camera 333. For this reason, in order to prevent such variations so as to securely specify the illumination region LA, the image processing device 410 performs image pickup by the CCD camera 333 a plurality of times, and averages the plurality of picked-up images.

Subsequently, in the illumination region LA thus specified, a distance AX in an X-axis direction of the illumination region LA, which is the length in the X-axis direction, a distance AY in a Y-axis direction of the illumination region LA, which is the length in the Y-axis direction, and a center CA of the illumination region, which is the center of the illumination region LA are acquired (processing S664).

To be more specific, first, in the rectangular illumination region LA, the XY coordinates of all pixels of the four portions of the four sides LA1 through LA4 that provide the end portions thereof are determined. Next, in the left side LA1 at the left in FIG. 20 out of the two sides LA1 and LA2 that are parallel in the Y-axis direction, the X coordinate showing a largest value (the rightmost X coordinate in the drawing) among the XY coordinates of all pixels making up the left side LA1 is determined. Meanwhile, in the right side LA2 at the right in FIG. 20, the X coordinate showing a smallest value (the leftmost X coordinate in FIG. 20) among the XY coordinates of all pixels making up the right side LA2 is determined.

Similarly, in the upper side LA3 at the top in the drawing out of the two sides LA3 and LA4 that are parallel in the X-axis direction, the Y coordinate showing a smallest value (the lowermost Y coordinate in FIG. 20) among the XY coordinates of all pixels making up the upper side LA3 is determined. Meanwhile, in the lower side LA4 at the bottom in FIG. 20, the Y coordinate showing a largest value (the uppermost Y coordinate in FIG. 20) among the XY coordinates of all pixels making up the lower side LA4 is determined.

Then, on the basis of the X coordinates in the opposing two sides LA1 and LA2, a distance AX in the X-axis direction of the illumination region LA that is the length in the X-axis direction is determined. Furthermore, on the basis of the Y coordinates in the opposing two sides LA3 and LA4, a distance AY in the Y-axis direction of the illumination region LA that is the length in the Y-axis direction is determined. In addition, on the basis of the XY coordinates or the like of the four apex portions in the rectangular illumination region LA, the illumination region center CA, which is the central XY coordinate of the illumination region LA, is acquired.

Next, in an illumination margin calculating unit 452, an illumination margin in the X-axis direction (proportionally divided value) that indicates the allowance of the illumination region LA in the X-axis direction with respect to the illuminated region PLA is calculated on the basis of the distance LX in the X-axis direction of the illuminated region PLA and the distance AX in the X-axis direction of the illumination region LA (Processing S665: Procedure to calculate an illumination margin). To be more specific, the calculation is performed according to expression 1 shown below.

Illumination margin in $X$-axis direction $= (AX-LX)/2$    Expression 1

First lens arrays 113 that are standard samples determined to be non-defective are prepared as many as about thirty units, and the illumination margins in the X-axis direction are calculated beforehand on the first lens arrays 113. The mean value of the approximately thirty illumination margins in the X-axis direction that are calculated as described above is defined as the standard value of the illumination margin in the X-axis direction. The illumination margin in the X-axis direction differs according to the type of projector; however, it is normally a value of about 0.5 mm to about 1.0 mm. The number of the non-defective first lens arrays 113 to be prepared does not have to be thirty; it may be an arbitrary number as long as the standard value can be defined as the standard value.

Such a standard value may be established in advance before the automatic inspection is carried out, and may be arranged such that it may be called up, as necessary, when the automatic inspection is performed.

Then, a pass/fail determining unit 454 compares the calculated illumination margin in the X-axis direction and a standard value to determine whether the calculated illumination margin in the X-axis direction is not less than the standard value (Processing S666: Procedure to determine pass/fail). As a result of the determination, if the calculated illumination margin in the X-axis direction is smaller than the standard value, then the test object is determined "defective" (processing S672). If the calculated illumination margin in the X-axis direction is not less than the standard value, then the system proceeds to subsequent processing S667.

Next, as described above, in the illumination margin calculating unit 452, an illumination margin in the Y-axis direction (proportionally divided value) that indicates the allowance of the illumination region LA in the Y-axis direction with respect to the illuminated region PLA is calculated on the basis of the distance LY in the Y-axis direction of the illuminated region PLA and the distance AY in the Y-axis direction of the illumination region LA (Processing S667: Procedure to calculate an illumination margin). To be more specific, the calculation is performed according to expression 2 shown below.

Illumination margin in $Y$-axis direction $= (AY-LY)/2$    Expression 2

As in the case of the illumination margin in the X-axis direction discussed above, the standard value of the illumination margin in the Y-axis direction is established in advance. As in the case of the illumination margin in the X-axis direction, the illumination margin in the Y-axis direction typically takes a value within a range of about 0.5 mm to about 1.0 mm, although it differs, depending on the type of projector.

Next, the pass/fail determining unit 454 compares the calculated illumination margin in the Y-axis direction and the standard value to determine whether the calculated illumination margin in the Y-axis direction is the standard value or more (Processing S668: Procedure to determine pass/fail). As a result of the determination, if the calculated illumination margin in the Y-axis direction is smaller than the standard value, then the test object is determined "defective" (processing S672). If the calculated illumination margin in the Y-axis direction is the standard value or more, then the system proceeds to subsequent processing S669.

Next, in a difference amount calculating unit 453, the amount of the central difference between centers CA and CL in the X-axis direction and the Y-axis direction is calculated on the basis of a calculated illumination region center CA and illuminated region center CL (Processing S669: Procedure to calculate a difference amount). At this time, the central difference amount in the X-axis direction is denoted as GX, while the central difference amount in the Y-axis direction is denoted as GY. Thus, the amount of the central difference between the centers CA and CL is represented as (GX, GY).

A difference amount in the X-axis direction LXN is calculated from the foregoing X coordinates of a left side PLA1 of the illuminated region PLA and a left side LA1 of the illumination region LA, and furthermore, a difference amount in the Y-axis direction LYN is calculated from the foregoing Y coordinates of an upper side PLA3 of the illuminated region PLA and an upper side LA3 of the illumination region LA (processing S670). The difference amounts in the respective axis directions LXN and LYN may alternatively be determined beforehand when the aforesaid illumination margins are determined.

As a result, these difference amounts LXN and LYN in the respective axis directions are determined on the basis of the aforesaid illumination margins.

Next, the pass/fail determining unit 454 determines whether a calculated central difference amount GX is not less than the difference amount in the X-axis direction LXN, and a calculated central difference amount GY is not less than the difference amount in the Y-axis direction LYN (Processing S671: Procedure for determining pass/fail).

As a result of the determination, if the calculated central difference amount GX is not less than the difference amount in the X-axis direction LXN and the central difference amount GY is not less than the difference amount in the Y-axis direction LYN, then the pass/fail determining unit 454 proceeds to processing S673. If the determination result is other than this, that is, if at least either a condition where the calculated central difference amount GX is smaller than the difference amount in the X-axis direction LXN, or a condition where the central difference amount GY is smaller than the difference amount in the Y-axis direction LYN is satisfied, then the test object is determined as "defective" (processing S672).

Then, a standard value for the central difference amount is set beforehand, and the pass/fail determining unit 454 determines whether the calculated central difference amounts (GX, GY) are not more than the standard value (Processing S673: Procedure to determine pass/fail). The standard value for the central difference amount can be set by inspecting about thirty non-defectives, as previously described. The standard value for the central difference amount can be also set by considering primarily the standard values for the foregoing illumination margins and the degree of possible misalignment of the first lens array 113 to be inspected when it is set on the holder 312. The standard value for the central difference amount is normally about 0.1 mm.

If the determination result indicates that the calculated central difference amounts (GX, GY) are larger than the standard value, then the test object is determined as "misaligned" (processing S674). If the calculated central difference amounts (GX, GY) are not more than the standard value, then the test object is determined as "non-defective" (processing S675).

Accordingly, if the central difference amount GX is the difference amount in the X-axis direction LXN or more and the predetermined standard value or less, and the central difference amount GY is the difference amount in the Y-axis direction LYN or more and the predetermined standard value or less at the same time, that is, if the central difference amounts GX, GY are within a predetermined range, then the test object is determined as "non-defective."

The pass/fail determination (processing S66) is carried out as described above. At this time, if the test object is determined as "non-defective" in processing S66, then as previously described, "OK 701" is shown on the display 401, or "NG 702" is shown on the display 401 if the test object is determined as "defective," as shown in FIG. 16.

As an alternative, if it is determined that the first lens array 113 has been misaligned, then the first lens array 113 may be re-mounted on the holder 312 and re-inspected to check whether it is truly "non-defective."

Thus, the pass/fail determination (processing S66) is terminated, and the automatic inspection is also terminated.

After completion of the automatic inspection described above, as shown in FIG. 9, the diverse types of data of the illumination margin in the X-axis direction (AX−LX)/2, the illumination margin in the Y-axis direction (AY−LY)/2, the central difference amounts (GX, GY), and the difference amounts in the respective axis directions LXN and LYN that have been calculated are stored in a hard disk or the like of the main unit 402 of the personal computer 400 (processing S7).

Each time the stored data reaches 1 Mbyte, a message telling that the data has reached 1 Mbyte appears on the display 401.

This completes the inspection of the first lens array 113.

<7> Effects of the Embodiment

According to the second embodiment, the following effects are obtained in addition to the same effects as those of (2) through (10) in the first embodiment.

(11) Automatic determination is performed on the basis of calculated illumination margins and central difference amounts GX and GY, so that the optical characteristics of the first lens array 113 can be easily inspected. Thus, the optical characteristics of the first lens array 113 can be inspected simply by mounting the first lens array 113 on the first lens array holder 312, so that the first lens array 113 does not have to be inspected after all components are assembled into a projector, as in the past. This makes it possible to reduce the load of the inspecting operation, and to control the manufacturing cost.

(12) The standard values for the illumination margin in the X-axis direction, the illumination margin in the Y-axis direction, and the central difference amount that cause the first lens array 113 to be determined defective due to misalignment are respectively established. Hence, in the pass/fail determining procedure (processing S666, processing S668, and processing S670), the first lens array 113 that has been determined defective due to misalignment can be securely determined on the basis of the calculated illumination margin in the X-axis direction, illumination margin in the Y-axis direction, and central difference amount. Thus, since the test objects that have been once determined defective can be accurately re-determined to be non-defective, thereby permitting an enhanced yield of the first lens array 113 to be achieved.

(13) If luminance change points are within the parting frame 171, and if the illumination margins in the X-axis direction and the Y-axis direction are found to be larger than the standard values and the central difference amounts GX and GY are found to be values within a predetermined range in the pass/fail determining procedure (the processing S666, the processing S668, the processing S671, and the processing S673), then the first lens array 113 is determined to be non-defective processing S673). Thus, pass/fail can be easily determined simply by establishing the standard values in advance.

(14) The first lens array 113 is determined to be misaligned (processing S674) when luminance change points are within the parting frame 171; the illumination margins in the X-axis direction and the Y-axis direction are found to be larger than the standard values; the central difference amount GX is found to be not less than the difference amount LXN in the X-axis direction; the central difference amount GY is found to be not less than the difference amount LYN in the Y-axis direction; and the central difference amounts GX and GY are found to be larger than predetermined standard values in the pass/fail determining procedure (the processing S666, the processing S668, the processing S671, and the processing S673). Thus, whether the first lens array 113 is simply misaligned can be reliably and easily determined merely by establishing the standard values in advance.

(15) The X-axis and Y-axis are set along the two sides orthogonal to each other in the illumination region LA and the illuminated region PLA, then the illumination margins in the respective axial directions along these X-axis and the Y-axis are calculated. Hence, the illumination margins can be easily calculated by relatively easy calculation.

(16) Furthermore, in the sides LA1 through LA4 in the illumination region LA, the distance AX in the X-axis direction and the distance AY in the Y-axis direction are set from the XY coordinates in which the illumination region LA is the smallest. This makes it possible to reliably identify the illumination region LA having a predetermined luminance value, allowing the illumination margins in the respective axial directions to be accurately calculated.

(17) To pick up the image of the illumination region LA, the image pickup operation is carried out a plurality of times, and the plurality of picked-up images is averaged, thereby restraining the variations in the XY coordinates of a specified illumination region LA. This permits improved accuracy of inspection results.

(18) The standard values of the illumination margins and the central difference amounts can be easily determined primarily by preparing and inspecting about thirty non-defective first lens arrays 113. Therefore, the standard values can be used as the basic data or the like when changing the design of the first lens array 113 or the projector 100.

<8> Modifications of the Embodiments

The present invention is not limited to the embodiments described above, and includes other constructions or the like that enable advantages of the present invention to be fulfilled. The modifications or the like shown below are also included in the present invention.

For instance, in the above embodiments, the parting frame 171 has been formed like marking-off on the ground glass 170. However, the parting frame 171 is not limited thereto. Alternatively, the parting frame 171 may be inscribed on the ground glass 170 by using a pen or the like, or a setting may be made such that the parting frame 171 appropriate to a selected type of projector is displayed on the display 401. The above embodiments, however, are advantageous in that they minimize the chances of erroneous setting and permit the range to be reliably specified.

The ground glass 170 has been adopted as the projection plate. However, the projection plate is not limited thereto, and it may be formed of a diverse types of plastic materials, such as acrylic material, or resins, or other materials, such as a commercially available transmissive screen.

In the embodiments discussed above, the image processor 330 has been provided. However, the image processor 330 is dispensable. Basically, any other construction may be acceptable as long as it allows the luminance values in the parting frame 171 to be checked so as to determine pass/fail. The embodiments, however, are advantageous in that they permit automatic, easy determination of pass/fail.

In the embodiments discussed above, the light source lamp 111A has used a halogen lamp. However, it is not limited thereto, and it may alternatively be a different type of lamp.

The light source device 320 has not been provided with a reflector. However, the reflector may be installed thereto.

The collimeter lens 112 and the light source lamp 111A are integrated into the light source device 320. However, they do not have to be integrated, in particular. The embodiments, however, are advantageous in that they can be disposed at once, thus saving time.

The light source device 320 has been constructed so that it may be moved forward/backward along the illumination optical axis. However, it may alternatively be constructed not to be moved forward/backward for improved type switching performance, or the light source device itself, for example, may be made switchable according to the type.

In the embodiments discussed above, the test object setting unit 317 formed of the integrated holders 312 through 315 has been provided. However, all the holders may not be integrated, or some holders, e.g., only the lens array holders 312 and 313, may be integrated. However, the embodiments discussed above is advantageous in that time-saving inspection can be accomplished.

In the embodiments described above, the test object has been the first lens array 113. However, the test object is not limited thereto, and it may alternatively be the second lens array 115. In such a case, a standard sample may be used for the first lens array 113.

Further alternatively, the standard samples may be used for the lens arrays 113 and 115 and the collimeter lens 112, and the superimposing lens 119 may be the test object. Thus, other illumination optical devices in addition to the first lens array 113 may be easily inspected, making it possible to restrain an increase in the manufacturing cost attributable to an inspecting operation.

In the embodiments discussed above, the number of the scanning lines 610 has been selectable. However, the number of the scanning lines 610 may alternatively be fixed. The above embodiments, however, are advantageous in that they allow changes according to test objects.

In the above embodiments, the scanning line inspection starts with the horizontal scanning lines 612; however, the scanning line inspection may alternatively be begun with the vertical scanning lines 611.

In the above embodiments, the lens arrays 113 and 115, which are test objects, are the optical devices constituting the integrator illumination optical system 110 of the projector 100, and the present invention, however, is not limited thereto. The lens arrays used for other applications may also be inspected by the inspecting device in accordance with the present invention.

In the above second embodiment, the illumination margin calculating procedure (processing S665 and S667) calculates the illumination margins on the basis of the distance AX in the X-axis direction and the distance AY in the Y-axis direction in the illuminated region PLA and the illumination region LA; however, the calculation method is not limited thereto. Alternatively, the illumination margins may be calculated on the basis of the number of pixels in the illumination region LA as the area of the illumination region LA and the number of pixels in the illuminated region PLA as the area of the illuminated region PLA. In such a case, there is an advantage in that the illumination margins can be easily calculated on the basis of the difference between the area of the illumination region LA and the area of the illuminated region PLA.

In the second embodiment, the pass/fail of the illumination margin in the X-axis direction is determined (the processing S666), and then the pass/fail of the illumination margin in the Y-axis direction is determined (the processing S667). Thereafter, the pass/fail of the central difference amount is determined (the processing S669). The order of these steps is not particularly restricted to this order. Basically, any order is acceptable as long as all these three steps of pass/fail determination are implemented.

In the second embodiment, the positions of the luminance change points are determined (the processing S65) first, and then the pass/fail determination steps (the processing S666, the processing S668, and the processing S670) are performed; the order, however, is not particularly restricted to this order.

In the second embodiment, the X-axis and the Y-axis have been set along the two sides orthogonal to each other PLA1 through PLA4, and LA1 through LA4 in the rectangular parting frame 171 and the rectangular illumination region LA. However, the orthogonal coordinate system may be established in other directions rather than being limited to the above directions. The embodiment, however, provides an advantage of easier arithmetic processing.

ADVANTAGES

As described above, according to the device to inspect illumination optical devices and the method to inspect illumination optical devices, a parting frame appropriate to an illumination region is formed. This arrangement makes it possible to determine a test object as defective if any portion that is darker than a design luminance is detected in the parting frame, thus permitting easy inspection of the optical characteristics of illumination optical devices. Therefore, the optical characteristics of illumination optical devices can be inspected merely by setting the illumination optical devices on holders, obviating the need to inspect the illumination optical devices after assembling all components into a projector with considerable efforts, as in the related art. This permits the load of the inspecting operation to be reduced and the manufacturing cost to be controlled.

The invention claimed is:

1. A method to inspect an illumination optical device by detecting a luminous flux emitted from a light source through the illumination optical device to inspect optical characteristics of the illumination optical device, comprising:

forming an optical image of the luminous flux emitted through the illumination optical device onto a projection plate on which a parting frame is formed in association with an illumination region of the illumination optical device;

capturing, by using an image pickup device and an image capturing device, the optical image formed by the optical image forming step;

acquiring a luminance value of the captured optical image;

acquiring a region, where the luminance value among the acquired luminance values is a preset luminance threshold value or more, as the illumination region of the optical image;

calculating an illumination margin on the basis of the acquired illumination region, which indicates the allowance of the illumination region with respect to an illuminated region, and the illuminated region defined by the parting frame;

calculating the amount of a difference between centers on the basis of the center of the illumination region obtained by the illumination region acquiring step, and the center of the illuminated region obtained by the parting frame; and determining whether the illumination optical device is non-defective or defective on the basis of the calculated illumination margin and the amount of the difference between the centers.

2. The method to inspect an illumination optical device according to claim 1, the pass/fail determining step determining that the illumination optical device is non-defective if the illumination margin is larger than a predetermined value and the amount of the difference between the centers is a value within a predetermined range.

3. The method to inspect an illumination optical device according to claim 1, the pass/fail determining step determining that the illumination optical device is misaligned if the illumination margin is larger than a predetermined range, and the amount of the difference between the centers is a value within the predetermined range.

4. The method for inspecting an illumination optical device according to claim 1, further including:

setting an orthogonal coordinate system formed of an X-axis and a Y-axis in a plane orthogonal to an illumination optical axis of the luminous flux, and the illumination margin calculating step calculating the illumination margin in the direction of the X-axis on the basis of the distance of the illumination region in the direction of the X-axis and the distance of the illuminated region in the direction of the X-axis, and calculating the illumination margin in the direction of the Y-axis on the basis of the distance of the illumination region in the direction of the Y-axis and the distance of the illuminated region in the direction of the Y-axis.

5. The method to inspect an illumination optical device according to claim 1, the illumination margin calculating step calculating the illumination margin on the basis of areas of the illumination region and the illuminated region.

* * * * *